US012590072B2

(12) United States Patent
von Geldern et al.

(10) Patent No.: US 12,590,072 B2
(45) Date of Patent: Mar. 31, 2026

(54) THYROMIMETICS

(71) Applicant: Autobahn Therapeutics, Inc., San Diego, CA (US)

(72) Inventors: Thomas von Geldern, Richmond, IL (US); Bradley Backes, San Francisco, CA (US)

(73) Assignee: AUTOBAHN THERAPEUTICS, INC., San Diego, CA (US)

( * ) Notice: Subject to any disclaimer, the term of this patent is extended or adjusted under 35 U.S.C. 154(b) by 339 days.

(21) Appl. No.: 18/002,035

(22) PCT Filed: Jun. 17, 2021

(86) PCT No.: PCT/US2021/037788

§ 371 (c)(1),
(2) Date: Dec. 15, 2022

(87) PCT Pub. No.: WO2021/257804

PCT Pub. Date: Dec. 23, 2021

(65) Prior Publication Data

US 2023/0242492 A1 Aug. 3, 2023

Related U.S. Application Data

(60) Provisional application No. 63/040,446, filed on Jun. 17, 2020.

(51) Int. Cl.

*C07D 253/075* (2006.01)
*C07C 39/367* (2006.01)
*C07D 261/12* (2006.01)

(52) U.S. Cl.

CPC ........ *C07D 253/075* (2013.01); *C07C 39/367* (2013.01); *C07D 261/12* (2013.01)

(58) Field of Classification Search

CPC .. C07D 235/075; C07D 261/12; C07C 39/367
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,652,441 | A | 3/1987 | Okada et al. |
| 4,675,189 | A | 6/1987 | Kent et al. |
| 4,677,191 | A | 6/1987 | Tanaka et al. |
| 4,723,027 | A | 2/1988 | Stoutamire et al. |
| 4,728,721 | A | 3/1988 | Yamamoto et al. |
| 4,741,897 | A | 5/1988 | Andrews et al. |
| 4,917,893 | A | 4/1990 | Okada et al. |
| 4,992,445 | A | 2/1991 | Lawter et al. |
| 5,001,139 | A | 3/1991 | Lawter et al. |
| 5,023,252 | A | 6/1991 | Hseih |
| 5,466,569 | A | 11/1995 | Eber et al. |
| 5,616,345 | A | 4/1997 | Geoghegan et al. |
| 5,883,294 | A | 3/1999 | Scanlan et al. |
| 6,054,485 | A | 4/2000 | Schwartz et al. |
| 6,107,517 | A | 8/2000 | Scanlan et al. |
| 6,236,946 | B1 | 5/2001 | Scanlan et al. |
| 6,441,015 | B2 | 8/2002 | Aspnes et al. |
| 6,787,652 | B1 | 9/2004 | Dow et al. |
| 7,288,571 | B2 | 10/2007 | Hangeland et al. |
| 7,302,347 | B2 | 11/2007 | Baxter et al. |
| 7,915,261 | B2 | 3/2011 | Ishii et al. |
| 7,919,494 | B2 | 4/2011 | Ishii et al. |
| 7,919,495 | B2 | 4/2011 | Ishii et al. |
| 9,562,012 | B2 | 2/2017 | Tanis et al. |
| 9,701,650 | B2 | 7/2017 | Scanlan et al. |
| 10,130,643 | B2 | 11/2018 | Cable et al. |
| 10,226,438 | B2 | 3/2019 | Scanlan et al. |
| 10,392,356 | B2 | 8/2019 | Scanlan et al. |
| 10,544,075 | B2 | 1/2020 | Scanlan et al. |
| 10,870,616 | B2 | 12/2020 | Scanlan et al. |
| 11,104,654 | B2 | 8/2021 | Scanlan et al. |
| 11,325,886 | B2 | 5/2022 | Scanlan et al. |
| 11,510,887 | B2 | 11/2022 | Scanlan et al. |
| 11,578,032 | B2 | 2/2023 | Scanlan |
| 11,613,517 | B2 | 3/2023 | Scanlan et al. |
| 11,780,825 | B2 | 10/2023 | Zhou et al. |
| 2003/0203898 | A1 | 10/2003 | Haning et al. |
| 2003/0215434 | A1 | 11/2003 | Khan et al. |
| 2004/0157844 | A1 | 8/2004 | Dow et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |

(Continued)

FOREIGN PATENT DOCUMENTS

| | | | |
|---|---|---|---|
| CN | 1882327 | A | 12/2006 |
| CN | 101180097 | A | 5/2008 |

(Continued)

OTHER PUBLICATIONS

Hashimoto, Bioorg & Med Chem, vol. 13, 2005, 3627-3639. (Year: 2005).*

Actis et al., Small molecule inhibitors of PCNA/PIP-box interaction suppress translesion DNA synthesis. Bioorg Med Chem. 21(7):1972-1977 (2013).

Alonso-Merino et al., Thyroid hormones inhibit TGF-beta signaling and attenuate fibrotic responses. PNAS USA 113(24):E3451-E3460 (2016).

Ashraf et al., Synthesis, characterization and in vitro hydrolysis studies of ester and amide prodrugs of dexibuprofen. Medicinal Chemistry Research 21:3361-3368 (2012).

Balkwill et al., Smoldering and polarized inflammation in the initiation and promotion of malignant disease. Cancer Cell 7(3):211-217 (2005).

(Continued)

*Primary Examiner* — D Margaret M Seaman

(74) *Attorney, Agent, or Firm* — WILSON SONSINI GOODRICH & ROSATI

(57) ABSTRACT

Disclosed herein are thyromimetic compounds having utility for treating diseases such as neurodegenerative disorders and fibrotic diseases. Pharmaceutical compositions containing such compounds are also provided, as are methods of their preparation.

20 Claims, No Drawings

(56) References Cited

U.S. PATENT DOCUMENTS

| | | | |
|---|---|---|---|
| 2008/0221170 | A1 | 9/2008 | Roberts et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0199309 | A1 | 7/2016 | Mousa et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2019/0210950 | A1 | 7/2019 | Scanlan et al. |
| 2020/0163930 | A1 | 5/2020 | Jerzak et al. |
| 2020/0181103 | A1 | 6/2020 | Scanlan et al. |
| 2020/0361849 | A1 | 11/2020 | Von Geldern et al. |
| 2020/0405669 | A1 | 12/2020 | Scanlan et al. |
| 2021/0002208 | A1 | 1/2021 | Scanlan |
| 2021/0053917 | A1 | 2/2021 | Von Geldern et al. |
| 2021/0087137 | A1 | 3/2021 | Scanlan et al. |
| 2021/0230146 | A1 | 7/2021 | Zhou et al. |
| 2023/0048992 | A1 | 2/2023 | von Geldern et al. |
| 2023/0242471 | A1 | 8/2023 | Von Geldern et al. |
| 2023/0242473 | A1 | 8/2023 | Von Geldern et al. |
| 2023/0348364 | A1 | 11/2023 | Backes et al. |

FOREIGN PATENT DOCUMENTS

| | | | | |
|---|---|---|---|---|
| CN | 101189248 | A | | 5/2008 |
| CN | 101547898 | A | | 9/2009 |
| CN | 101600450 | A | | 12/2009 |
| CN | 101610774 | A | | 12/2009 |
| CN | 101848712 | A | | 9/2010 |
| CN | 107848940 | A | | 3/2018 |
| EP | 1148054 | B1 | | 11/2005 |
| EP | 3259246 | A1 | | 12/2017 |
| JP | S59116256 | A | | 7/1984 |
| JP | H09301917 | A | | 11/1997 |
| JP | 2004512303 | A | | 4/2004 |
| JP | 2004517037 | A | | 6/2004 |
| JP | 2008542301 | A | | 11/2008 |
| JP | 2008545711 | A | | 12/2008 |
| JP | 2012106996 | A | | 6/2012 |
| JP | 2016517884 | A | | 6/2016 |
| PE | 20180021 | A1 | | 1/2018 |
| RU | 2007148927 | A | | 7/2009 |
| WO | WO-9321146 | A1 | | 10/1993 |
| WO | WO-9900353 | A1 | | 1/1999 |
| WO | WO-0039077 | A2 | | 7/2000 |
| WO | WO-0073292 | A1 | | 12/2000 |
| WO | WO-0160784 | A1 | | 8/2001 |
| WO | WO-0190053 | A1 | | 11/2001 |
| WO | WO-0200167 | A2 | | 1/2002 |
| WO | WO-0234260 | A1 | | 5/2002 |
| WO | WO-02072539 | A1 | | 9/2002 |
| WO | WO-02081426 | A1 | | 10/2002 |
| WO | WO-2004043939 | A1 | | 5/2004 |
| WO | WO-2006031922 | A2 | | 3/2006 |
| WO | WO-2006128056 | A2 | | 11/2006 |
| WO | WO-2006128058 | A2 | | 11/2006 |
| WO | WO-2007110226 | A1 | | 10/2007 |
| WO | 2007/132475 | | * | 11/2007 |
| WO | WO-2007132475 | A1 | | 11/2007 |
| WO | WO-2008125724 | A1 | | 10/2008 |
| WO | WO-2013006734 | A1 | | 1/2013 |
| WO | WO-2014078892 | A1 | | 5/2014 |
| WO | WO-2014178892 | A1 | | 11/2014 |
| WO | WO-2014178931 | A1 | | 11/2014 |
| WO | WO-2015188015 | A1 | | 12/2015 |
| WO | WO-2016134292 | A1 | | 8/2016 |
| WO | WO-2017015360 | A1 | | 1/2017 |
| WO | WO-2017201320 | A1 | | 11/2017 |
| WO | WO-2018032012 | A1 | | 2/2018 |
| WO | WO-2018208707 | A1 | | 11/2018 |
| WO | WO-2019160980 | A1 | | 8/2019 |
| WO | 2020/117962 | | * | 6/2020 |
| WO | WO-2020117962 | A1 | | 6/2020 |
| WO | WO-2020118564 | A1 | | 6/2020 |
| WO | WO-2020123861 | A1 | | 6/2020 |
| WO | WO-2020169069 | A1 | | 8/2020 |
| WO | WO-2020180624 | A1 | | 9/2020 |
| WO | WO-2020227549 | A1 | | 11/2020 |
| WO | WO-2021108549 | A1 | | 6/2021 |
| WO | WO-2021247847 | A1 | | 12/2021 |
| WO | WO-2021257804 | A1 | | 12/2021 |
| WO | WO-2021257834 | A1 | | 12/2021 |
| WO | WO-2021257851 | A1 | | 12/2021 |

OTHER PUBLICATIONS

Bastin et al. Salt selection and optimisation procedures for pharmaceutical new chemical entities. Organic Process Research & Development 4(5):427-435 (2000).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Belikov. Pharmaceutical Chemistry: Manual. Moscow: MEDpress-inform (pp. 27-29) (2007).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. PNAS USA 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24:1-13 (2004).

Boger et al., Fatty acid amide hydrolase substrate specificity. Bioorg Med Chem Lett. 10(23):2613-2616 (2000).

Borngraeber et al. Ligand Selectivity by Seeking Hydrophobicity in Thyroid Hormone Receptor. PNAS USA 100(26):15358-15363 (2003).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

Cravatt et al., Supersensitivity to anandamide and enhanced endogenous cannabinoid signaling in mice lacking fatty acid amide hydrolase. Proc Natl Acad Sci U S A 98(16):9371-9376 (2001).

(56) References Cited

OTHER PUBLICATIONS

Dell'Acqua et al., Functional and molecular evidence of myelin- and neuroprotection by thyroid hormone administration in experimental allergic encephalomyelitis. Neuropathol Appl Neurobiol. 38(5):454-470 (2012).
Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Elbers et al. Thyroid Hormone Mimetics: the Past, Current Status and Future Challenges. Cur Atheroscler Rep 18(3):14 (2016).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. PNAS USA 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Hashimoto et al., Design and synthesis of complementing ligands for mutant thyroid hormone receptor TRbeta(R320H): a tailor-made approach toward the treatment of resistance to thyroid hormone. Bioorg Med Chem. 13(11):3627-3639 (2005).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Jorgensen. Thyroid hormones and analogues. II. Structure—activity relationships. Hormonal Proteins and Peptides; Li, C. H., Ed.; Academic Press: New York 6:107-204 (1978).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult CNS. J Neurosci. 32(36):12528-12542 (2012).
Krogsgaard-Larsen et al. Chapter 4: Design and application of prodrugs. Textbook of Drug Designing and Discovery, US, Taylor & Francis Inc (3rd Ed.) (pp. P460-P514). (2002).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).
Martin et al. The proliferating cell nuclear antigen regulates retinoic acid receptor transcriptional activity through direct protein-protein interaction. Nucleic Acids Res. 33(13):4311-21 (2005).
Massague. TGFbeta signalling in context. Nat Rev Mol Cell Biol. 13(10):616-630 (2012).
Meinig et al., Structure-activity relationships of central nervous system penetration by fatty acid amide hydrolase (FAAH)-targeted thyromimetic prodrugs. ACS Med Chem Lett. 10(1):111-116 (2018).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'SHEA et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
Patani et al. Bioisosterism: A Rational Approach in Drug Design. Chem. Rev. 96:3147-3176 (1996).
PCT/CN2018/120634 International Search Report and Written Opinion dated Sep. 11, 2019.
PCT/US2016/018732 International Search Report and Written Opinion dated Jun. 1, 2016.
PCT/US2017/033388 International Search Report and Written Opinion dated Aug. 16, 2017.
PCT/US2019/017881 International Search Report and Written Opinion dated May 13, 2019.
PCT/US2019/019576 International Search Report and Written Opinion dated May 13, 2019.
PCT/US2019/066066 International Search Report and Written Opinion dated Mar. 5, 2020.
PCT/US2020/020199 International Search Report and Written Opinion dated May 14, 2020.

(56) References Cited

OTHER PUBLICATIONS

PCT/US2020/062229 International Invitation to Pay Additional Fees dated Jan. 27, 2021.
PCT/US2020/062229 International Search Report and Written Opinion dated Mar. 24, 2021.
PCT/US2021/035679 International Invitation to Pay Additional Fees dated Aug. 16, 2021.
PCT/US2021/035679 International Search Report and Written Opinion dated Oct. 29, 2021.
PCT/US2021/037788 International Invitation to Pay Additional Fees dated Aug. 30, 2021.
PCT/US2021/037788 International Search Report and Written Opinion dated Nov. 10, 2021.
PCT/US2021/037833 International Invitation to Pay Additional Fees dated Aug. 30, 2021.
PCT/US2021/037833 International Search Report and Written Opinion dated Nov. 17, 2021.
PCT/US2021/037862 International Invitation to Pay Additional Fees dated Aug. 30, 2021.
PCT/US2021/037862 International Search Report and Written Opinion dated Nov. 17, 2021.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
Pubchem Compound Record for CID 140404356, 2-[3,5-Dichloro-4-[(2-chloro-4-hydroxyphenyl)methyl]phenyl]-4,5-dihydro-1,2,4-triazin-3-one; https://pubchem.ncbi.nlm.nih.gov/compound/140404356 (2019).
Pubchem Compound Record for CID 142030791, 4-[(2,6-Dimethyl-4-pyrrolidin-1-ylphenyl)methyl]-2-propan-2-ylphenol; https://pubchem.ncbi.nlm.nih.gov/compound/142030791 (2019).
PubChem SID 235918886 [ https://pubchem.ncbi.nlm.nih.gov/substance/ 235918886] (2015).
PubChem SID 319635332 [ https://pubchem.ncbi.nlm.nih.gov/substance/319635332 ] (2016).
Pubmed Compound Record for CID 132562601, 2-(4-(3-(1-(2H3)Methyl-(2,2,2-2H3)ethyl)-4-hydroxybenzyl)-3,5-dlmethylphenoxy)acetic acid. U.S. National Library of Medicine https://pubchem.ncbi.nlm.nih.gov/compound/132562601 (2018).
Pubmed Compound Record for CID 132562602, 2-(4-(3-Isopropyl-4-hydroxy(alpha-3H)benzyl)-3,5-dimethylphenoxy)acetic acid. U.S. National Library of Medicine https://pubchem.ncbi.nlm.nih.gov/compound/132562602 (2018).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
Scanlan. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70:6789-6795 (2014).
Taub et al., Lipid lowering in healthy volunteers treated with multiple doses of MGL-3196, a liver-targeted thyroid hormone receptor-beta agonist. Atherosclerosis 230(2):373-380 (2013).
Tegeli et al. Synthesis and evaluation of amide prodrugs of mefenamic acid. International Journal of Chemical Sciences 12(3):1033-1043, (2014).
Thyroid. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/ updated Mar. 1, 2021].
Valadares et al. Role of halogen bonds in thyroid hormone receptor selectivity: pharmacophore-based 3D-QSSR studies. J Chem Inf Model 49(11):2606-2616 (2009).
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: a brief review. 3(3):62-64 (2013).
Ye et al., Thyroid receptor ligands. 1. Agonist ligands selective for the thyroid receptor beta1. J Med Chem. 46(9):1580-1588 (2003).
Yen., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).
Lian, Brian, et al. Compositions comprising thyroid hormone receptor beta (TRB) agonists for the treatment of fibrosis and inflammation: CA Doc No. 173:90753, 1-2 (2020).

* cited by examiner

THYROMIMETICS

CROSS-REFERENCE

This application claims benefit of U.S. Provisional Patent Application No. 63/040,446, filed on Jun. 17, 2020, which is incorporated herein by reference in its entirety.

BACKGROUND

Technical Field

The invention relates to thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calža et al., *Brain Res Revs* 48:339-346, 2005). However, TH is not an acceptable long-term therapy due to the limited therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm et al., *Mini Rev Med Chem* 7:79-86, 2007). These receptors are expressed in two major forms with heterogenous tissue distributions and overlapping but distinct sets of target genes (Yen, *Physiol Rev* 81:1097-1142, 2001). TRα is enriched in the heart, brain, and bone while TRβ is enriched in the liver (O'Shea et al., *Nucl Recept Signal* 4:e011, 2006).

It has also been reported that TH can inhibit the transforming growth factor beta (TGF-β) signaling, and, therefore, attenuate fibrotic responses (Alonso-Merino et al., *Proc Natl Acad Sci USA.* 113(24):E3451-60, 2016). TGF-β is a cytokine with pleiotropic effects in tissue homeostasis that plays a key role in pathological processes such as fibrosis (Massagué, *Nat Rev Mol Cell Biol.* 13(10):616-630, 2012). By inhibiting TGF-β signalling, TR ligands or agonists could have beneficial effects to block the progression of fibrotic diseases, such as idiopathic pulmonary fibrosis (IPF) or systemic sclerosis (Varga et al., *Curr Opin Rheumatol.* 20(6):720-728, 2008).

Developing selective thyromimetics has been challenging due to the high sequence homology of thyroid hormone receptor subtypes; namely, only one amino acid residue on the internal surface of the ligand binding domain cavity varies between the α1 and β1 forms. Despite this challenge, several groups have reported TRβ-selective agonists. Scanlan et al. identified GC-1 (sobetirome) as one of the first potent analogs to demonstrate significant TRβ-selectivity in vitro (Chiellini et al., *Chem Biol* 5:299-306, 1998; Yoshihara et al., *J Med Chem* 46:3152-3161, 2003) and in vivo (Trost et al., *Endocrinology* 141:3057-3064, 2000; Grover et al., *Endocrinology* 145:1656-1661, 2004; Baxter et al., *Trends Endocrinol Metab* 15:154-157, 2004). As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Metabasis employs a similar core with a novel liver-targeting prodrug strategy in MB07811 (Erion et al., *PNAS* 104(39), 15490-15495, 2007). Madrigal has reported TRβ-selective activity in vivo for MGL-3196 (Taub et al., *Atherosclerosis* 230(2):373-380, 2013). KaroBio has reported on eprotirome (KB2115; Berkenstam et al., *PNAS* 105(2):663-668, 2008) and KB-141 (Ye et al., *J Med Chem* 46:1580-1588, 2003), both of which demonstrate improved TRβ-selectivity in vitro. Further studies from this group highlight additional selective compounds (Hangeland et al., *BMCL* 14:3549-3553, 2004). Two TRβ-selective agonists, identified as SKL-12846 and SKL-13784, have been reported to accumulate in the liver and to reduce cholesterol levels in rodents (Takahashi et al., *BMC* 22(1):488-498, 2014; *Xenobiotica* 2015, 1-9). Kissei has also reported selective compounds (Shiohara et al., *BMC* 20(11), 3622-3634, 2012).

While progress has been made in this field, there remains a need in the art for further selective thyromimetic compounds, as well as to products containing the same, and for methods related to their use and preparation.

BRIEF SUMMARY

Disclosed herein are compounds according to Formula I:

(I)

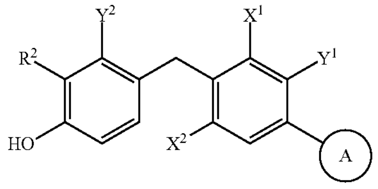

or a pharmaceutically acceptable isomer, racemate, tautomer, hydrate, solvate, isotope, or salt thereof, wherein A, $X^1$, $X^2$, $Y^1$, $Y^2$, and $R^2$ are as defined below.

In an embodiment, a pharmaceutical composition is provided comprising a compound having the structure of Formula (I), or a pharmaceutically acceptable isomer, racemate, tautomer, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis. In another embodiment, the pharmaceutical composition is for use in treating a medical condition associated increased activity of TGF-β, such as a fibrotic disease.

In an embodiment, a method is provided for treating a neurodegenerative disorder in a subject in need thereof, comprising administering a compound having the structure of Formula (I), or a pharmaceutically acceptable salt or composition comprising the same. In some aspects, the neurodegenerative disorder can be classified as a demyelinating disease such as X-linked adrenoleukodystrophy or multiple sclerosis.

In another embodiment, a method is provided for treating a medical condition associated with over-expression of TGF-β in a subject in need thereof, comprising administering a compound having the structure of Formula (I), or a pharmaceutically acceptable salt or composition comprising the same. In some aspects, the medical condition associated with over-expression of TGF-β is a fibrotic disease.

DETAILED DESCRIPTION

As mentioned above, the invention relates to thyromimetic compounds, to products comprising the same, and to methods for their use and synthesis.

In one embodiment, compounds are provided having the structure of Formula (I):

(I)

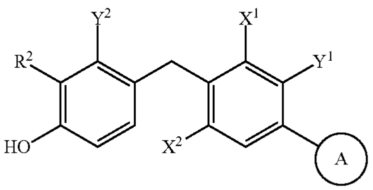

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —S(O)$_2$R' or —S(O)$_2$OR';

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^2$ is lower alkyl, lower alkenyl, carbocycle, heterocycle, carbocyclealkyl, or heterocyclealkyl, wherein $R^2$ is optionally substituted with one or more halo, lower alkyl, lower haloalkyl, —CN, —OR', —NR'R", =O, =S, —S(O)$_2$R' or —S(O)$_2$OR'; and R' and R" are each, independently, H, lower alkyl, or lower haloalkyl;

wherein when $R^2$ is isopropyl and $X^1$ and $X^2$ are each methyl, A is not thiazolidinedione.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of straight chain lower alkyl groups include, but are not limited to, methyl, ethyl, n-propyl, n-butyl, n-pentyl-, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "lower alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, isopropenyl, butenyl, pentenyl, and hexenyl.

As used herein, "lower alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of lower alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined herein with one or more hydrogen atoms replaced with halogen. Examples of lower haloalkyl groups include, but are not limited to, —$CF_3$, —$CHF_2$, and the like.

"Lower alkoxy" refers to a lower alkyl as defined herein joined by way of an oxygen atom (i.e., —O-(lower alkyl). Examples of lower alkoxy groups include, but are not limited to, methoxy, ethoxy, n-propoxy, n-butoxy, isopropoxy, sec-butoxy, tert-butoxy, and the like.

"Lower haloalkoxy" refers to a lower haloalkyl as defined herein joined by way of an oxygen atom (i.e., —O-(lower haloalkyl). Examples of lower haloalkoxy groups include, but are not limited to, —$OCF_3$, —$OCHF_2$, and the like.

"Carbocyclyl," "carbocycle," or "carbocyclic" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined herein. In another embodiment, carbocycle includes aryl as defined herein.

"Carbocyclealkyl" are alkyl groups as defined herein in which a hydrogen or carbon bond of the alkyl group is replaced with a bond to a carbocycle group as defined herein. In one embodiment, carbocyclealkyl includes cycloalkylalkyl. In one embodiment, carbocyclealkyl includes arylalkyl. Examples of carbocyclealkyl groups include, but are not limited to, cyclopropylmethyl, cyclobutylmethyl, benzyl, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Cycloalkylalkyl" are alkyl groups as defined herein in which a hydrogen or carbon bond of the alkyl group is replaced with a bond to a cycloalkyl group as defined herein.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Arylalkyl" are alkyl groups as defined herein in which a hydrogen or carbon bond of the alkyl group is replaced with a bond to an aryl group as defined herein.

"Heterocyclyl," "heterocycle," or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclealkyl" are alkyl groups as defined herein in which a hydrogen or carbon bond of the alkyl group is replaced with a bond to a heterocycle group as defined herein. In one embodiment, heterocyclealkyl includes heteroarylalkyl.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

"Heteroarylalkyl" are alkyl groups as defined herein in which a hydrogen or carbon bond of the alkyl group is replaced with a bond to a heteroaryl group as defined herein.

In one embodiment, compounds are provided having the structure of Formula (II):

(II)

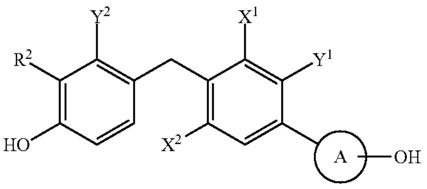

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —$S(O)_2R'$ or —$S(O)_2OR'$;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^2$ is lower alkyl, lower alkenyl, carbocycle, heterocycle, carbocyclealkyl, or heterocyclealkyl, wherein $R^2$ is optionally substituted with one or more halo, lower alkyl, lower haloalkyl, —CN, —OR', —NR'R", =O, =S, —$S(O)_2R'$ or —$S(O)_2OR'$; and R' and R" are each, independently, H, lower alkyl, or lower haloalkyl;

wherein when $R^2$ is isopropyl and $X^1$ and $X^2$ are each methyl, A is not thiazolidinedione.

In one embodiment, compounds are provided having the structure of Formula (I) or Formula (II), or a pharmaceutically acceptable isomer, racemate, tautomer, hydrate, solvate, isotope, or salt thereof, wherein $R^2$ is lower alkyl optionally substituted with one or more halo, —CN, —OR', —NR'R", =O, =S, —$S(O)_2R'$ or —$S(O)_2OR'$, wherein R' and R" are each, independently, H, lower alkyl, or lower haloalkyl. In another embodiment, $R^2$ is unsubstituted lower alkyl. In a more specific embodiment, $R^2$ is methyl, ethyl, propyl, isopropyl, or butyl. In one embodiment, $R^2$ is isopropyl.

In one embodiment, compounds are provided having the structure of Formula (III):

(III)

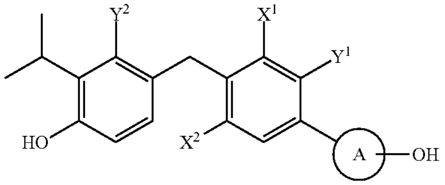

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —$S(O)_2R'$ or —$S(O)_2OR'$;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

R' and R" are each, independently, H, lower alkyl, or lower haloalkyl;

wherein when $X^1$ and $X^2$ are each methyl, A is not thiazolidinedione.

In one embodiment, compounds are provided having the structure of Formula (I) or Formula (II), or a pharmaceutically acceptable isomer, racemate, tautomer, hydrate, solvate, isotope, or salt thereof, wherein $R^2$ is carbocyclealkyl or heterocyclealkyl. In one embodiment, compounds are provided having the structure of Formula (I) or Formula (II), or a pharmaceutically acceptable isomer, racemate, tautomer, hydrate, solvate, isotope, or salt thereof, wherein $R^2$ is arylalkyl or heteroarylalkyl.

In one embodiment, compounds are provided having the structure of Formula (IV):

(IV)

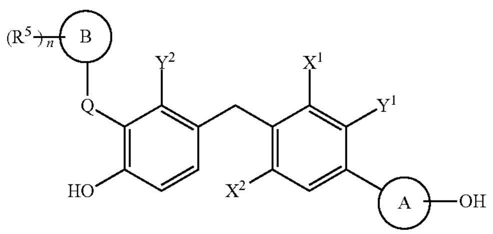

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R'', =O, =S, —$S(O)_2$R' or —$S(O)_2$OR';

R' and R'' are each, independently, H, lower alkyl, or lower haloalkyl;

B is aryl or heteroaryl;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

Q is —$C(R^3R^4)$— or —$\{C(R^3R^4)\}_2$—;

$R^3$ and $R^4$ are at each occurrence, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^3$, $R^4$, $R^5$, $R^a$, and $R^b$ are each, independently, optionally substituted with one or more halo, —CN, —OR', —NR'R'', =O, =S, —$S(O)_2$R' or —$S(O)_2$OR'.

In one embodiment, compounds are provided having the structure of Formula (V):

(V)

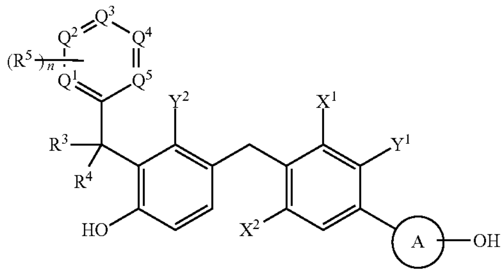

or a pharmaceutically acceptable isomer, racemate, tautomer, hydrate, solvate, isotope, or salt thereof, wherein:

$Q^1$, $Q^2$, $Q^3$, $Q^4$, and $Q^5$ are each, independently, CH, $CR^5$, or N;

A is carbocycle or heterocycle, wherein A is optionally substituted with one or more halo, lower alkyl, lower haloalkyl, —CN, —OR', —NR'R'', =O, =S, —$S(O)_2$R' or —$S(O)_2$OR';

R' and R'' are each, independently, H, lower alkyl, or lower haloalkyl;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^3$ and $R^4$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^3$, $R^4$, $R^5$, $R^a$, and $R^b$ are each, independently, optionally substituted with one or more halo, —CN, —OR', —NR'R'', =O, =S, —$S(O)_2$R' or —$S(O)_2$OR'.

In one embodiment, compounds are provided having the structure of Formula (V), or a pharmaceutically acceptable isomer, racemate, tautomer, hydrate, solvate, isotope, or salt thereof, wherein $Q^1$, $Q^2$, $Q^3$, $Q^4$, and $Q^5$ are each, independently, CH or $CR^5$. In one embodiment, compounds are provided having the structure of Formula (V), or a pharmaceutically acceptable isomer, racemate, tautomer, hydrate, solvate, isotope, or salt thereof, wherein at least one of $Q^1$, $Q^2$, $Q^3$, $Q^4$, or $Q^5$ is N. In one embodiment, compounds are provided having the structure of Formula (V), or a pharmaceutically acceptable isomer, racemate, tautomer, hydrate, solvate, isotope, or salt thereof, wherein at least two of $Q^1$, $Q^2$, $Q^3$, $Q^4$, and $Q^5$ are N.

In one embodiment, compounds are provided having the structure of Formula (VI):

(VI)

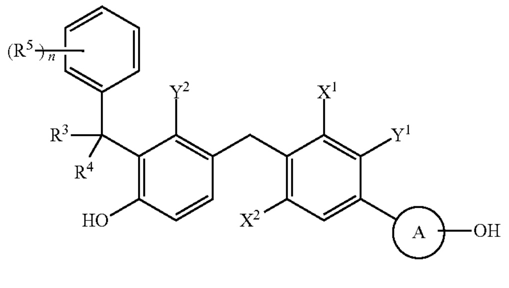

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —$S(O)_2$R' or —$S(O)_2$OR';

R' and R" are each, independently, H, lower alkyl, or lower haloalkyl;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^3$ and $R^4$ are each, independently, H, halo, —CN, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^3$, $R^4$, $R^5$, $R^a$, and $R^b$ are each, independently, optionally substituted with one or more halo, —CN, —OR', —NR'R", =O, =S, —$S(O)_2$R' or —$S(O)_2$OR'.

In one embodiment, compounds are provided having the structure of Formula (I) or Formula (II), or a pharmaceutically acceptable isomer, racemate, tautomer, hydrate, solvate, isotope, or salt thereof, wherein $R^2$ is carbocyle or heterocycle. In one embodiment, compounds are provided having the structure of Formula (I) or Formula (II), or a pharmaceutically acceptable isomer, racemate, tautomer, hydrate, solvate, isotope, or salt thereof, wherein $R^2$ is aryl or heteroaryl.

In one embodiment, compounds are provided having the structure of Formula (VII):

(VII)

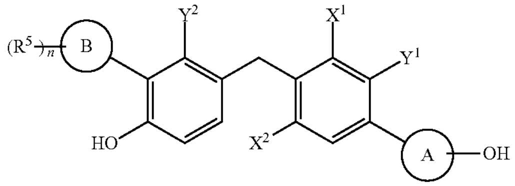

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —$S(O)_2$R' or —$S(O)_2$OR';

R' and R" are each, independently, H, lower alkyl, or lower haloalkyl;

B is aryl or heteroaryl;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^5$, $R^a$, and $R^b$ are each, independently, optionally substituted with one or more halo, —CN, —OR', —NR'R", =O, =S, —$S(O)_2$R' or —$S(O)_2$OR'.

In one embodiment, compounds are provided having the structure of Formula (VII), or a pharmaceutically acceptable isomer, racemate, tautomer, hydrate, solvate, isotope, or salt thereof, wherein B is carbocycle. In one embodiment, compounds are provided having the structure of Formula (VII), or a pharmaceutically acceptable isomer, racemate, tautomer, hydrate, solvate, isotope, or salt thereof, wherein B is aryl. In one embodiment, compounds are provided having the structure of Formula (VII), or a pharmaceutically acceptable isomer, racemate, tautomer, hydrate, solvate, isotope, or salt thereof, wherein B is phenyl.

In one embodiment, compounds are provided having the structure of Formula (VIII):

(VIII)

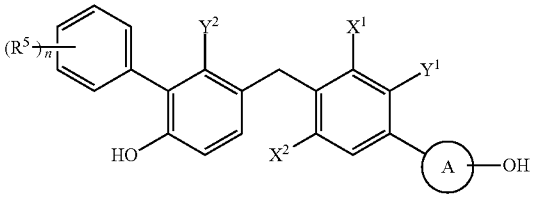

or a pharmaceutically acceptable isomer, racemate, tautomer, hydrate, solvate, isotope, or salt thereof, wherein:

A is carbocycle or heterocycle, wherein A is optionally substituted with one or more halo, lower alkyl, lower haloalkyl, —CN, —OR', —NR'R", =O, =S, —$S(O)_2$R' or —$S(O)_2$OR';

R' and R" are each, independently, H, lower alkyl, or lower haloalkyl;

X is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

each $R^5$ is, independently, halo, —CN, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

n is 0-5; and $R^a$ and $R^b$ are each, independently, H, lower alkyl, or lower haloalkyl;

wherein $R^5$, $R^a$, and $R^b$ are each, independently, optionally substituted with one or more halo, —CN, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is carbocycle optionally substituted with one or more halo, lower alkyl, lower haloalkyl, —CN, —OR', —NR'R", =O, =S, —$S(O)_2R'$ or —$S(O)_2OR'$, wherein R' and R" are each, independently, H, lower alkyl, or lower haloalkyl. In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is aryl optionally substituted with one or more halo, lower alkyl, lower haloalkyl, —CN, —OR', —NR'R", =O, =S, —$S(O)_2R'$ or —$S(O)_2OR'$, wherein R' and R" are each, independently, H, lower alkyl, or lower haloalkyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is phenyl optionally substituted with one or more halo, lower alkyl, lower haloalkyl, —CN, —OR', —NR'R", =O, =S, —$S(O)_2R'$ or —$S(O)_2OR'$, wherein R' and R" are each, independently, H, lower alkyl, or lower haloalkyl. In one embodiment, A is phenyl optionally substituted with one or more halo. In one embodiment, A is phenyl optionally substituted with one or more —CN. In one embodiment, A is phenyl optionally substituted with one or more —OR', wherein each R' is independently, H, lower alkyl, or lower haloalkyl. In one embodiment, A is phenyl optionally substituted with one or more —OR', wherein each R' is independently, H, lower alkyl, or lower haloalkyl and at least one R' is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is phenol or substituted phenol. In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is:

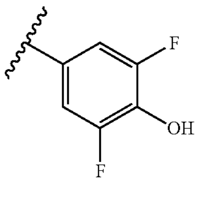

or

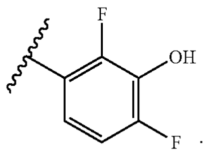

.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is heterocycle optionally substituted with one or more halo, lower alkyl, lower haloalkyl, —CN, —OR', —NR'R", =O, =S, —$S(O)_2R'$ or —$S(O)_2OR'$, wherein R' and R" are each, independently, H, lower alkyl, or lower haloalkyl. In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is heteroaryl optionally substituted with one or more halo, lower alkyl, lower haloalkyl, —CN, —OR', —NR'R", =O, =S, —$S(O)_2R'$ or —$S(O)_2OR'$, wherein R' and R" are each, independently, H, lower alkyl, or lower haloalkyl. In one embodiment, A is triazinyl, pyridinyl, pyrimidinyl, pyrazinyl, triazinyl, pyrrolyl, imidazolyl, thiazolyl, oxazolyl, isothiazolyl, isoxazolyl, oxadiazolyl, or thiadiazolyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein A is:

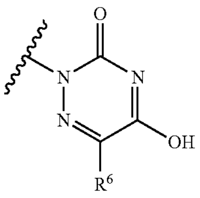

or

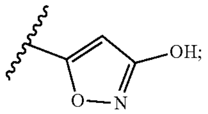

$R^6$ is H or —CN.

and

In one embodiment, compounds are provided having the structure of any one of Formula (IV), Formula (V), or Formula (VI), or a pharmaceutically acceptable isomer, racemate, tautomer, hydrate, solvate, isotope, or salt thereof, wherein $R^3$ is H.

In one embodiment, compounds are provided having the structure of any one of Formula (IV), Formula (V), or Formula (VI), or a pharmaceutically acceptable isomer, racemate, tautomer, hydrate, solvate, isotope, or salt thereof, wherein $R^3$ is carbocycle. In one embodiment, $R^3$ is cyclopropyl or cyclobutyl.

In one embodiment, compounds are provided having the structure of any one of Formula (IV), Formula (V), or Formula (VI), or a pharmaceutically acceptable isomer, racemate, tautomer, hydrate, solvate, isotope, or salt thereof, wherein $R^3$ is lower alkyl. In one embodiment, $R^3$ is methyl, ethyl, or propyl.

In one embodiment, compounds are provided having the structure of any one of Formula (IV), Formula (V), or Formula (VI), or a pharmaceutically acceptable isomer, racemate, tautomer, hydrate, solvate, isotope, or salt thereof, wherein $R^3$ is —$OR^a$. In one embodiment, $R^a$ is H. In one embodiment, R is lower alkyl. In one embodiment, R is lower methyl.

In one embodiment, compounds are provided having the structure of any one of Formula (IV), Formula (V), or Formula (VI), or a pharmaceutically acceptable isomer, racemate, tautomer, hydrate, solvate, isotope, or salt thereof, wherein $R^4$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is lower alkyl. In one embodiment, $X^1$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is halo. In one embodiment, $X^1$ is Cl or Br. In one embodiment, $X^1$ is Cl. In one embodiment, $X^1$ is Br.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^1$ is lower haloalkyl. In one embodiment, $X^1$ is —$CH_2F$, —$CHF_2$, or —$CF_3$. In one embodiment, $X^1$ is —$CF_3$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein X is lower alkenyl. In one embodiment, $X^1$ is vinyl or isopropenyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower alkyl. In one embodiment, $X^2$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is halo. In one embodiment, $X^2$ is Cl or Br. In one embodiment, $X^2$ is Cl. In one embodiment, $X^2$ is Br.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower haloalkyl. In one embodiment, $X^2$ is —$CHF_2$ or —$CF_3$. In one embodiment, $X^2$ is —$CF_3$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $X^2$ is lower alkenyl. In one embodiment, $X^2$ is vinyl or isopropenyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is lower alkyl. In one embodiment, $R^5$ is lower alkyl substituted with —OR'. In one embodiment, R' is H. In one embodiment, R' is lower alkyl. In one embodiment, R' is methyl, ethyl, or propyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is lower haloalkyl. In one embodiment, at least one $R^5$ is —$CH_2F$, —$CHF_2$, or —$CF_3$. In one embodiment, at least one $R^5$ is —$CF_3$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$OR^a$. In one embodiment, $R^a$ is lower alkyl. In one embodiment, $R^a$ is methyl, ethyl, or propyl. In one embodiment, $R^a$ is lower haloalkyl. In one embodiment, $R^a$ is —$CHF_2$ or —$CF_3$.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$C(O)R^a$. In one embodiment, $R^a$ is lower alkyl. In one embodiment, $R^a$ is methyl, ethyl, or propyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$NR^aC(O)R^b$. In one embodiment, $R^a$ is H and $R^b$ is lower alkyl. In one embodiment, $R^a$ is H and $R^b$ is methyl, ethyl, or propyl. In one embodiment, $R^a$ is H and $R^b$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$C(O)OR^a$. In one embodiment, $R^a$ is lower alkyl. In one embodiment, $R^a$ is methyl, ethyl, or propyl. In one embodiment, $R^a$ is methyl. In one embodiment, $R^a$ is ethyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —$S(O)_2R^a$. In one embodiment, $R^a$ is lower alkyl. In one embodiment, $R^a$ is methyl, ethyl, or propyl. In one embodiment, $R^a$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is halo. In one embodiment, at least one $R^5$ is F.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein at least one $R^5$ is —CN.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is halogen. In one embodiment, $Y^1$ is F. In one embodiment, $Y^1$ is Cl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is —CN.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkyl. In one embodiment, $Y^1$ is methyl, ethyl, or propyl. In one embodiment, $Y^1$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkoxy. In one embodiment, $Y^1$ is methoxy or ethoxy. In one embodiment, $Y^1$ is methoxy.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is halogen. In one embodiment, $Y^2$ is F. In one embodiment, $Y^2$ is Cl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is —CN.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is lower alkyl. In one embodiment, $Y^2$ is methyl, ethyl, or propyl. In one embodiment, $Y^2$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is lower alkoxy. In one embodiment, $Y^2$ is methoxy or ethoxy. In one embodiment, $Y^2$ is methoxy.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is F and $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is Cl and $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is —CN and $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkyl and $Y^2$ is H. In one embodiment, $Y^1$ is methyl and $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is lower alkoxy and $Y^2$ is H. In one embodiment, $Y^1$ is methoxy and $Y^2$ is H.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is F.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is Cl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is —CN.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is lower alkyl. In one embodiment, $Y^1$ is H and $Y^2$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is H and $Y^2$ is lower alkoxy. In one embodiment, $Y^1$ is H and $Y^2$ is methyl.

In one embodiment, compounds are provided having the structure of any one of Formula (I), Formula (II), Formula (III), Formula (IV), Formula (V), Formula (VI), Formula (VII), or Formula (VIII), or a pharmaceutically acceptable isomer, racemate, tautomer, hydrate, solvate, isotope, or salt thereof, wherein $Y^1$ is F and $Y^2$ is F.

Representative compounds of Formula (I), and Formulas (II) through (VIII) as applicable, include the compounds listed in Table 1 below, as well as pharmaceutically acceptable salts thereof. To this end, representative compounds are identified herein by their respective "Compound Number", which is sometimes abbreviated as "Compound No.", "Cmpd. No." or "No."

TABLE 1

| Representative Compounds | | |
|---|---|---|
| Cmpd No | Structure | Name |
| 1 | 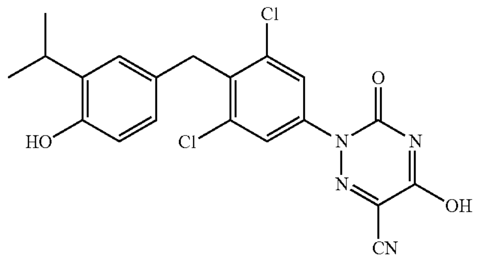 [SMILES: CC(C)c1cc(Cc2c(Cl)cc(-n3nc(C#N)c(O)nc3=O)cc2Cl)ccc1O] | 2-(3,5-dichloro-4-(4-hydroxy-3-isopropylbenzyl)phenyl)-5-hydroxy-3-oxo-2,3-dihydro-1,2,4-triazine-6-carbonitrile |
| 2 | 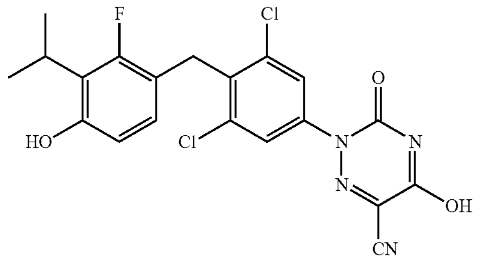 | 2-(3,5-dichloro-4-(2-fluoro-4-hydroxy-3-isopropylbenzyl)phenyl)-5-hydroxy-3-oxo-2,3-dihydro-1,2,4-triazine-6-carbonitrile |
| 3 | 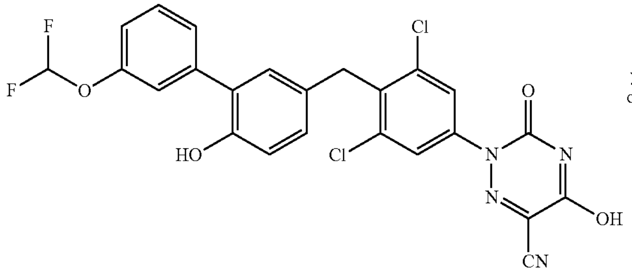 | 2-(3,5-dichloro-4-((3'-(difluoromethoxy)-6-hydroxy-[1,1'-biphenyl]-3-yl)methyl)phenyl)-5-hydroxy-3-oxo-2,3-dihydro-1,2,4-triazine-6-carbonitrile |
| 4 | 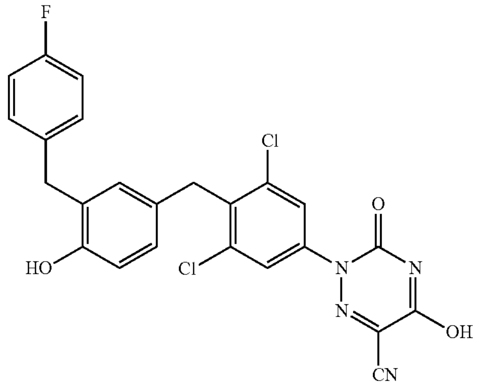 | 2-(3,5-dichloro-4-(3-(4-fluorobenzyl)-4-hydroxybenzyl)phenyl)-5-hydroxy-3-oxo-2,3-dihydro-1,2,4-triazine-6-carbonitrile |
| 5 | 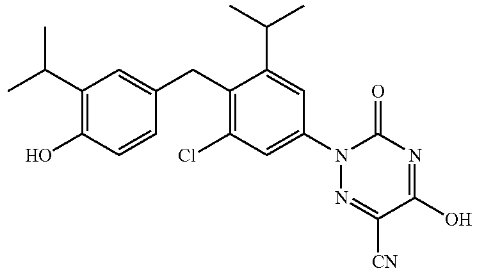 | 2-(3-chloro-4-(4-hydroxy-3-isopropylbenzyl)-5-isopropylphenyl)-5-hydroxy-3-oxo-2,3-dihydro-1,2,4-triazine-6-carbonitrile |

TABLE 1-continued

| Representative Compounds | | |
|---|---|---|
| Cmpd No | Structure | Name |
| 6 | 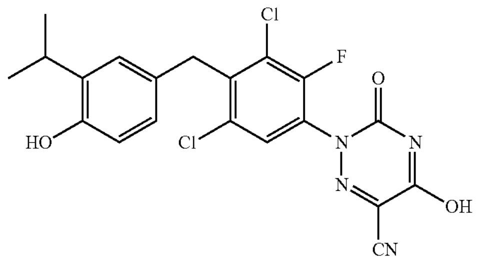 | 2-(3,5-dichloro-2-fluoro-4-(4-hydroxy-3-isopropylbenzyl)phenyl)-5-hydroxy-3-oxo-2,3-dihydro-1,2,4-triazine-6-carbonitrile |
| 7 | 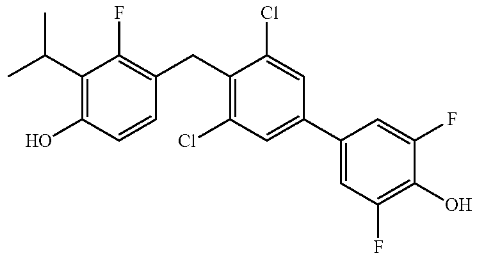 | 3',5'-dichloro-3,5-difluoro-4'-(2-fluoro-4-hydroxy-3-isopropylbenzyl)-[1,1'-biphenyl]-4-ol |
| 8 | 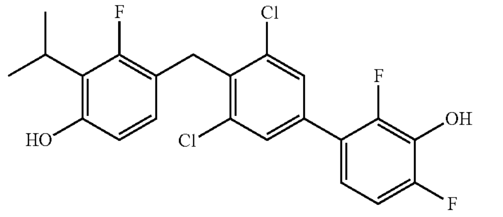 | 3',5'-dichloro-2,4-difluoro-4'-(2-fluoro-4-hydroxy-3-isopropylbenzyl)-[1,1'-biphenyl]-3-ol |
| 9 | 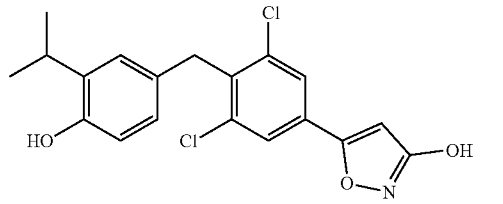 | 5-(3,5-dichloro-4-(4-hydroxy-3-isopropylbenzyl)phenyl)isoxazol-3-ol |
| 10 | 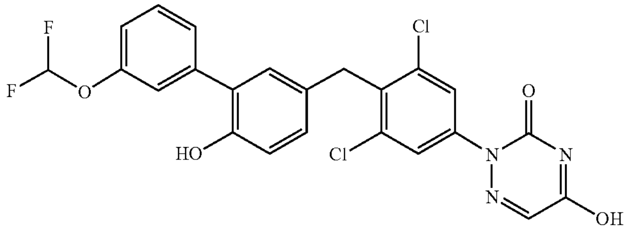 | 2-(3,5-dichloro-4-((3'-(difluoromethoxy)-6-hydroxy-[1,1'-biphenyl]-3-yl)methyl)phenyl)-5-hydroxy-1,2,4-triazin-3(2H)-one |

"Isomer" is used herein to encompass al chiral, diastereomenic or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms “racemate” and “racemic mixture” refer to an equal mixture of two enantiomers. A racemate is labeled “(±)” because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A “tautomer” refers to each of two or more structural isomers that readily interconvert in equilibrium by migration of an atom or group within the molecule. A tautomer commonly arises from a proton shift from one atom of a molecule to another atom of the same molecule. The present invention includes tautomers of compounds of Formula (I). For example, tautomers of isoxazolol and hydroxytriazinone are shown below:

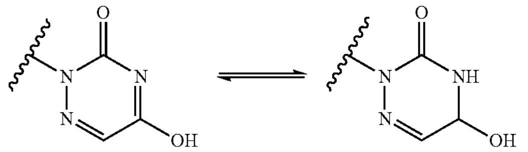

and

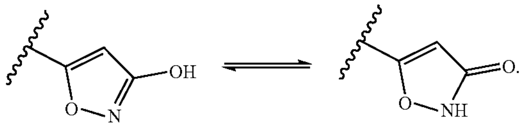

A “hydrate” is a compound that exists in combination with water molecules. The combination can include water in stoichiometric quantities, such as a monohydrate or a dihydrate, or can include water in random amounts. As the term is used herein a “hydrate” refers to a solid form; that is, a compound in a water solution, while it may be hydrated, is not a hydrate as the term is used herein.

A “solvate” is similar to a hydrate except that a solvent other that water is present. For example, methanol or ethanol can form an “alcoholate”, which can again be stoichiometric or non-stoichiometric. As the term is used herein a “solvate” refers to a solid form; that is, a compound in a solvent solution, while it may be solvated, is not a solvate as the term is used herein.

“Isotope” refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

“Salt” generally refers to an organic compound, such as a carboxylic acid or an amine, in ionic form, in combination with a counter ion. For example, salts formed between acids in their anionic form and cations are referred to as “acid addition salts”. Conversely, salts formed between bases in the cationic form and anions are referred to as “base addition salts.”

The term “pharmaceutically acceptable” refers an agent that has been approved for human consumption and is generally non-toxic. For example, the term “pharmaceutically acceptable salt” refers to nontoxic inorganic or organic acid and/or base addition salts (see, e.g., Lit et al., Salt Selection for Basic Drugs, *Int. J. Pharm.,* 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), tromethamine (tris-hydroxymethyl methylamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, tautomer, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy,* 21' Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, tautomer, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcelluloFse, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the *Physicians' Desk Reference*, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the neurodegenerative disease is a demyelinating disease. In another embodiment, the demyelinating disease is a chronic demyelinating disease. In yet another embodiment, the demyelinating disease is or is associated with a X-linked genetic disorder, leukodystrophy, dementia, tauopathy, or ischaemic stroke. In another embodiment, the demyelinating disease is or is associated with adult Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome. In one embodiment, the demyelinating disease is or is associated with multiple sclerosis, MCT8 deficiency, X-linked adrenoleukodystrophy (ALD), amyotrophic lateral sclerosis (ALS), Alzheimer's disease, frontotemporal dementia, or lacunar stroke.

As used herein, the term "neurodegenerative disease" refers to any type of disease that is characterized by the progressive deterioration of the nervous system.

As used herein, the term "demyelinating disease" refers to any disease or medical condition of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected.

An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

In yet another embodiment, a method of treating a subject having a X-linked genetic disorder is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the X-linked genetic disorder is MCT8 deficiency or X-linked adrenoleukodystrophy (ALD).

In another embodiment, a method of treating a subject having a leukodystrophy is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the leukodystrophy is adrenoleukodystrophy (ALD), adrenomyeloneuropathy (AMN), cerebral form of adrenoleukodystrophy (cALD), metachromatic leukodystrophy (MLD), Canavan's disease, or Krabbe disease (globoid leukodystrophy). As used herein, the term "adrenomyeloneuropathy" or "AMN" refers to an adult variant of X-linked adrenoleukodystrophy, characterized by ABCD1 gene mutation, that results in impaired peroxisome function with accumulation of very long chain fatty acids (VLCFA) and demyelination.

In one embodiment, a method of treating a subject having a tauopathy is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the tauopathy is Alzheimer's disease, frontotemporal dementia, primary age-related tauopathy (PART), Pick's disease, or frontotemporal dementia and parkinsonism linked to chromosome 17 (FTDP-17).

In yet another embodiment, a method of treating a subject having an ischaemic stroke is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the ischaemic stroke is lacunar stroke (also called "lacunar infarct"). In another embodiment, the present method is used to treat a subject suffering from a lacunar stroke syndrome (LACS).

In another embodiment, a method of treating a subject having adult Refsum disease, infantile Refsum disease, Alexander disease, Alzheimer's disease, balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In one embodiment, the demyelinating disease is multiple sclerosis. In another embodiment, the demyelinating disease is X-linked adrenoleukodystrophy (ALD).

In another embodiment, a method of treating a subject having an amyotrophic lateral sclerosis (ALS) disease is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the ALS is sporadic or familial ALS, or ALS with Superoxide dismutase-1 mutation.

In one embodiment, a method of treating a subject having a medical condition associated with increased activity of TGF-β is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof. In one embodiment, the medical condition associated with increased activity of TGF-β is a fibrotic disease. In another embodiment, the fibrotic disease is or is associated with nonalcoholic steatohepatitis (NASH), idiopathic pulmonary fibrosis (IPF), systemic scleroderma, or Alport syndrome. As used herein, the term "Alport syndrome" refers to a hereditary disorder caused by mutations in the a3a4a5(IV) collagen network genes resulting in structural defects in the glomerular basement membrane (GBM) early during development leading subsequently to the breakdown of the filtration barrier, development of renal fibrosis and kidney failure.

As used herein, the term "fibrotic disease" refers to a condition, disease or disorder that is amenable to treatment by administration of a compound having anti-fibrotic activity. Fibrotic diseases include, but are not limited to, pulmonary fibrosis, including idiopathic pulmonary fibrosis (IPF) and pulmonary fibrosis from a known etiology, liver fibrosis, and renal-fibrosis. Other exemplary fibrotic diseases include musculoskeletal fibrosis, cardiac fibrosis, post-surgical adhesions, scleroderma, glaucoma, and skin lesions such as keloids.

In another embodiment, a method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD) is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having IPF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pleuroparenchymal fibroelastosis, unclassifiable idiopathic interstitial pneumonias, hypersensitivity pneumonitis, radiation-induced lung injury, progressive massive fibrosis—pneumoconiosis, bronchiectasis, byssinosis, chronic respiratory disease, chronic obstructive pulmonary disease (COPD), emphysema, pulmonary arterial hypertension (PAH), or Cystic fibrosis is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having scleroderma/systemic sclerosis, graft versus host disease, hypertrophic scars, keloids, nephrogenic systemic fibrosis, porphyria cutanea tarda, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents. GvHD induced fibrosis, Scleredema adultorum, Lipodermatosclerosis, or Progeroid disorders (progeria, acrogeria, Werner's syndrome) is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having atrial fibrosis, endomyocardial fibrosis, cardiac fibrosis, atherosclerosis, restenosis, or arthrofibrosis is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having mediastinal fibrosis, myelofibrosis, post-polycythermia vera myelofibrosis, or post essential thrombocythemia is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having endometrial fibrosis, uterine fibroids, or Peyronie's disease is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having macular degeneration, diabetic retinopathy, retinal fibrovascular diseases, or vitreal retinopathy is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

In another embodiment, a method of treating a subject having scarring associated with trauma (surgical complications, chemotherapeutics drug-induced fibrosis, radiation induced fibrosis) is provided, the method comprising administering to the subject a pharmaceutically effective amount of a compound having the structure of Formula (I) or pharmaceutically acceptable isomer, racemate, tautomer, hydrate, solvate, isotope or salt thereof, or a pharmaceutical composition thereof.

As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "chronic" refers to a medical disorder or condition that persists over time or is frequently recurring.

Compounds having the structure of Formulas (I), and Formulas (II) through (VIII) as applicable, can be synthesized using synthetic techniques set forth in Schemes 1-5 below.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures, or higher if reactions are run in sealed vessels). A given reaction may be carried out in one solvent or a mixture of more than one solvent. Depending on the particular reaction, suitable solvents for a particular work-up following the reaction may be employed.

Scheme 1

Scheme 1

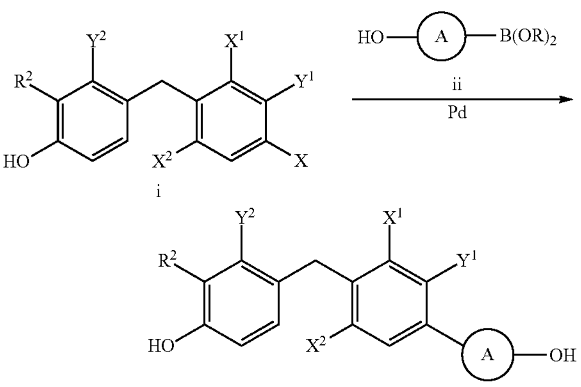

Compounds of the present invention (A=aryl or heteroaryl) can be prepared according to the methods described in Scheme 1. According to Scheme 1, intermediates like i (X=Br or I or OTf or the like) containing an active leaving group may be coupled with aryl- or heteroaryl-boronates like ii under standard Suzuki coupling conditions to give compounds of the present invention.

Scheme 2

Scheme 2

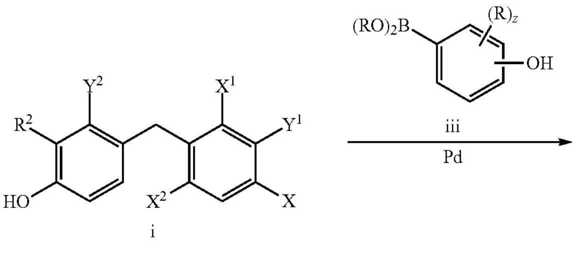

-continued

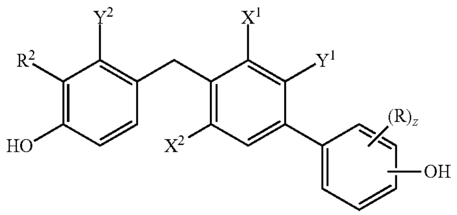

iv

For the specific case where A is aryl, compounds of the present invention can be prepared according to the methods of Scheme 2. According to Scheme 2, intermediates like i (X═Br or I or OTf or the like) can be coupled with substituted phenol-boronic acids like iii, using a palladium catalyst like $Pd(dppf)Cl_2$ or $Pd(PPh_3)_2$ or the like, with a base like $NaHCO_3$ or $K_2CO_3$ or the like, in a solvent like THF or 1,4-dioxane and water or alcohol or the like, optionally with heating, to produce hydroxyphenyl derivatives iv.

Scheme 3

Scheme 3

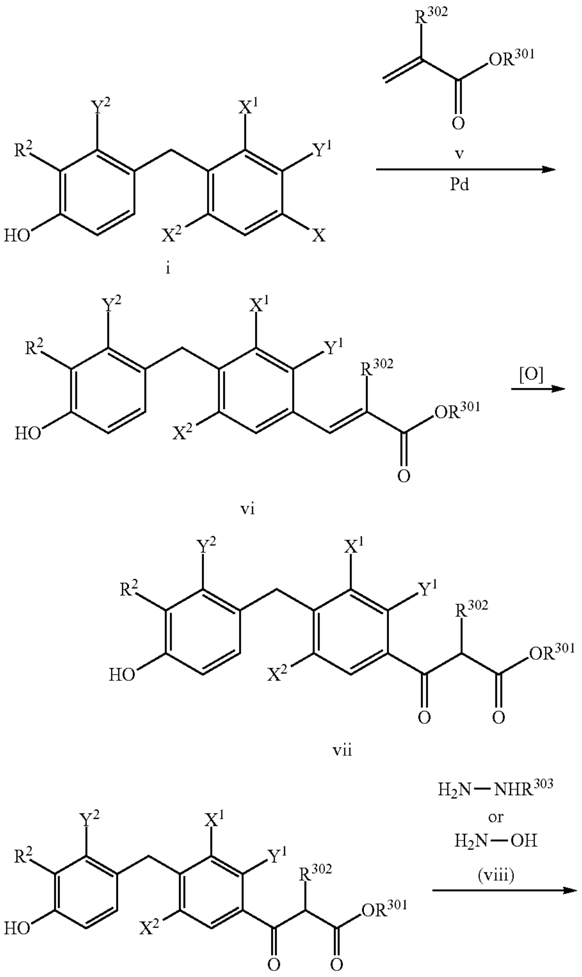

i, vi, vii, vii

-continued

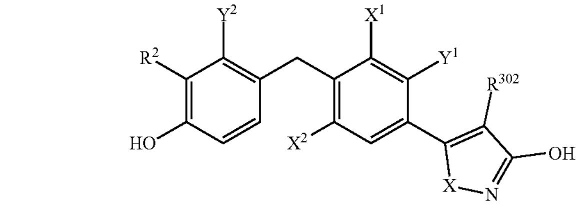

ix

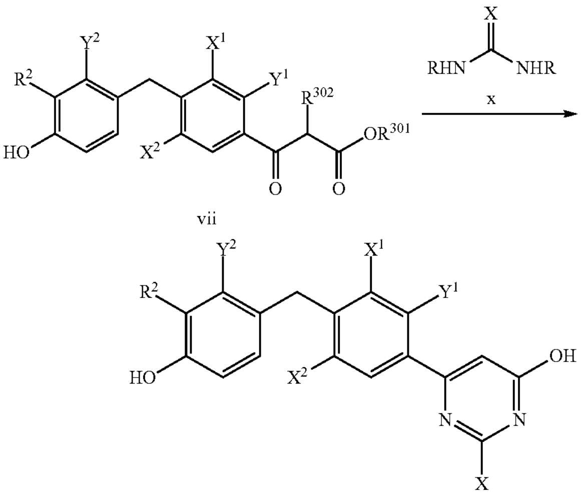

vii, xi

Compounds of the present invention can also be prepared from intermediates like i through stepwise assembly of the heterocyclic moiety, as demonstrated in Scheme 3. According to Scheme 3, intermediates like i can be converted to cinnamates like vi by coupling with acrylates like v using a palladium catalyst. Oxidation of the olefinic moiety of vi provides beta-ketoesters like vii. Condensation of vii with hydrazines viii or hydroxylamine generates the corresponding hydroxypyrazoles (ix, X═$NR^{303}$) or hydroxyisoxazoles (ix, X═O). Alternatively 7 may be condensed with ureas (x, X═O) or amidines (x, X═$NR^{304}$) to generate hydroxpyrimidines xi.

Scheme 4

Scheme 4

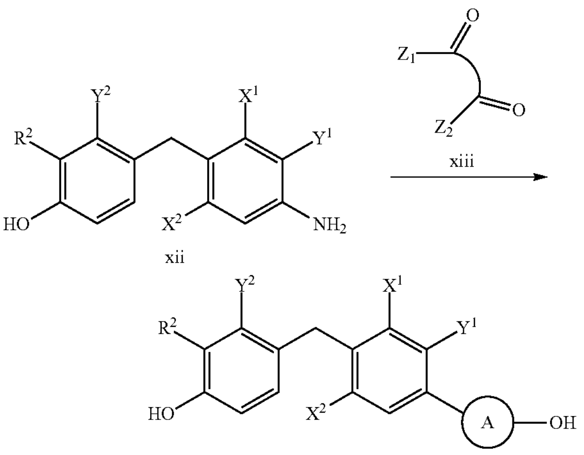

xii

-continued

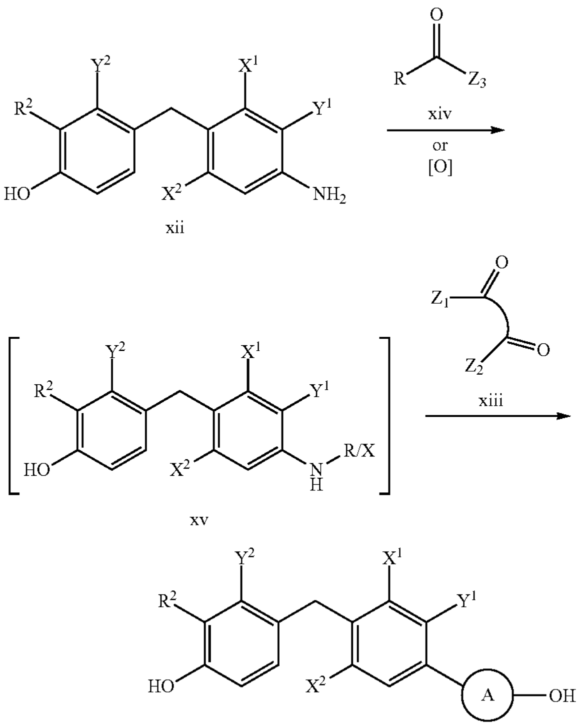

xii xv

Where A is an N-linked heterocycle, compounds of the present invention can be prepared according to the methods of Scheme 4. According to Scheme 4, anilines like xii can be reacted with bifunctional acylating agents xiii to provide heterocycles A directly. Alternatively, anilines xii may first be reacted with a carbonyl equivalent like xiv or with an oxidizing agent, to give an intermediate like xv, which is then condensed with a bifunctional acylating agent like xiii to provide heterocycles A.

Scheme 5

Scheme 5

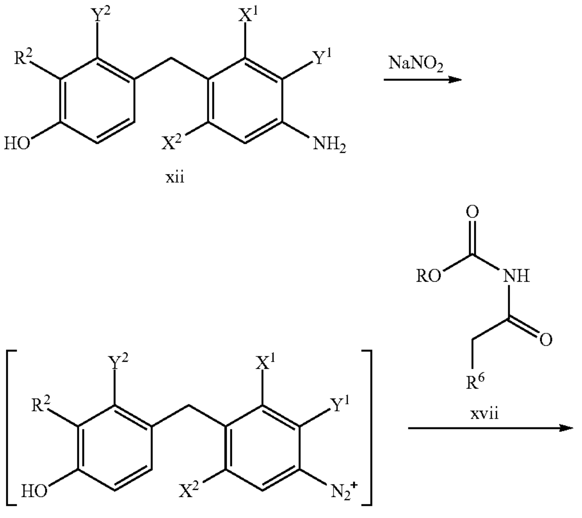

xii xvi

-continued

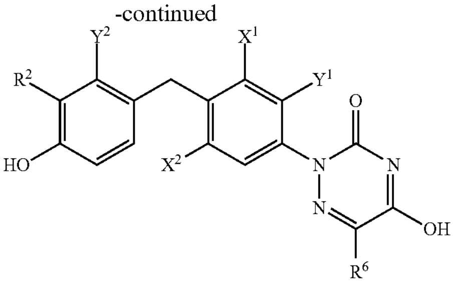

Where A is 1,2,4-triazine, compounds of the present invention can be prepared according to the methods of Scheme 5. According to Scheme 5, anilines like xii are first N-nitrated using a nitrosating agent like sodium nitrite or the like, in a solvent like water or ethanol or the like. The intermediate diazonium salt compound xvi is reacted with a bifunctional acylating reagent xvii like ethyl N-(2-cyano-acetyl)carbamate or the like, in a solvent system including water or alcohol or the like and a base like pyridine or triethylamine or the like, with heating if necessary, to give a 1,2,4-triazine product like xviii.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC (normal-phase or reversed-phase) using methods as described. Preparative HPLC purification by reverse phase HPLC was performed using gradients of acetonitrile in aqueous TFA or an equivalent HPLC system such as Methanol in aqueous ammonium acetate.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays.

It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^{1}H$ Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Chemical names were generated using the ChemDraw naming software (Version 17.0.0.206) by PerkinElmer Informatics, Inc. In some cases, generally accepted names and generally accepted acronyms for commercially available reagents were used in place of names generated by the naming software.

Intermediate A1

Synthesis of N,N-dibenzyl-3,5-dichloroaniline (Intermediate A1)

A1

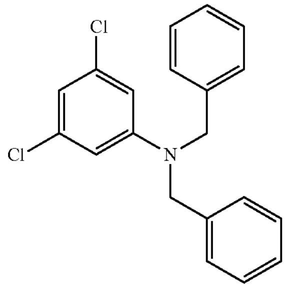

To a solution of 3,5-dichloroaniline (20.0 g, 123 mmol) in DMF (100 mL) at 0° C. was added sodium hydride powder (8.5 g, 370 mmol) in portions to control gas evolution. The mixture was stirred at rt for 1 h. Benzyl bromide (63.3 g, 370 mmol) was added dropwise, and the resultant mixture was stirred at rt overnight. The mixture was poured slowly into water (1000 mL) with stirring, then extracted with EtOAc (300 mL*3). The combined organic layer was washed with water (500 mL*2) and brine (300 mL), dried over $Na_2SO_4$ and concentrated in vacuo. The crude product was purified by silica gel column chromatography (pet. ether/EtOAc=100:1) to afford Intermediate A1 (40.0 g, 94.7% yield) as a yellow solid.

TLC: Pet. ether/EtOAc=5/1 (v/v), Rf=0.8

$^{1}H$ NMR: (400 MHz, DMSO-$d_6$) δ 7.37-7.32 (m, 4H), 7.28-7.23 (m, 6H), 6.67 (t, J=1.6 Hz, 1H), 6.62 (d, J=1.6 Hz, 2H), 4.74 (s, 4H).

Intermediate A2

Synthesis of 2,6-dichloro-4-(dibenzylamino)benzaldehyde (Intermediate A2)

A2

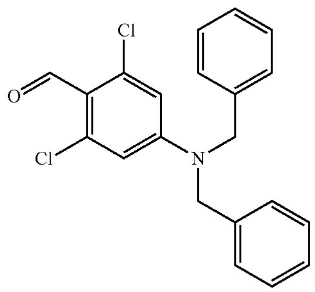

Phosphorus oxychloride (56.8 g, 368 mmol) was added dropwise to DMF (200 mL) at 0° C. The mixture was warmed to rt and stirred for 1 h. A solution of Intermediate A1 (42 g, 12 mmol) in DMF (50 mL) was added. The mixture was heated to 80° C. for 5 h. The reaction mixture was poured into ice-water (1 L), and the pH was adjusted to pH-7 with aq. $NaHCO_3$. The mixture was extracted with EtOAc (200 mL*3). The combined organic layer was washed with water (200 mL), and brine (300 mL), dried over $Na_2SO_4$ and concentrated in vacuo to afford Intermediate A2 (38.5 g, 84.7% yield) as a yellow solid.

TLC: Pet. ether/EtOAc=5/1 (v/v), Rf=0.6

$^{1}H$ NMR: (400 MHz, DMSO-$d_6$) δ 10.13 (s, 1H), 7.40-7.36 (m, 4H), 7.31-7.25 (m, 6H), 6.80 (s, 2H), 4.88 (s, 4H).

Intermediate A3

Synthesis of (2,6-dichloro-4-(dibenzylamino)phenyl)methanol (Intermediate A3)

A3

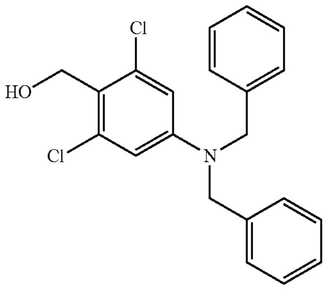

To a solution of Intermediate A2 (20 g, 54 mmol) in THF (100 mL) at 5° C. was added $NaBH_4$ (2.7 g, 70 mmol) in portions. The mixture was stirred at rt for 2 h. Water (300 mL) was added and the resultant mixture was extracted with EtOAc (200 mL*2). The combined organic layer was washed with brine (300 mL), dried over $Na_2SO_4$ and concentrated in vacuo to afford Intermediate A3 (20 g, 99% yield) as a yellow solid.

TLC: Pet. ether/EtOAc=5/1 (v/v), Rf=0.7

$^1$H NMR: (400 MHz, DMSO-$d_6$) δ 7.39-7.31 (m, 4H), 7.28-7.20 (m, 6H), 6.66 (s, 2H), 4.84 (t, J=5.2 Hz, 1H), 4.75 (s, 4H), 4.49 (d, J=5.2 Hz, 2H).

Intermediate A4

Synthesis of N,N-dibenzyl-3,5-dichloro-4-(chloromethyl)aniline (Intermediate A4)

A4

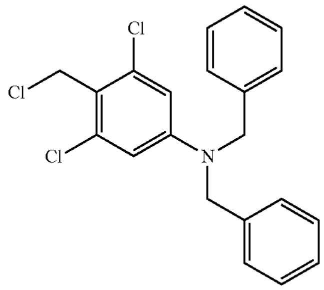

To a solution of Intermediate A3 (2.4 g, 6.5 mmol) in DCM (20 mL) at 0° C. was added $SOCl_2$ (1.6 g, 13 mmol). The mixture was stirred at rt for 2 h. The mixture was concentrated in vacuo and the crude Intermediate A4 was used without further purification.

TLC: Pet. ether/EtOAc=10/1 (v/v), Rf=0.5

Intermediate A5

Synthesis of N,N-dibenzyl-3-bromo-5-chloroaniline (Intermediate A5)

A5

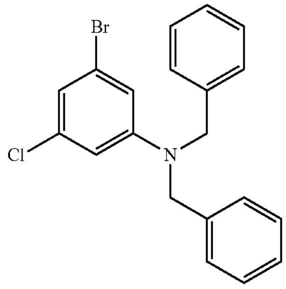

A solution of 3-bromo-5-chloroaniline (10.2 g, 49.4 mmol) and benzyl bromide (16.9 g, 98.8 mmol) in DMF (100 mL) was cooled to 0° C. NaH (5.93 g of 60% oil dispersion, 148 mmol) was added in portions to control gas evolution. The reaction mixture was stirred at rt overnight. Water (500 mL) was added carefully; the resultant mixture was extracted with EtOAc (200 mL*2). The combined organic phase was washed with water (500 mL), and brine (500 mL), dried over $Na_2SO_4$, and concentrated in vacuo. The residue was washed with EtOAc/hexane: 1/10 (50 mL); the resultant solid was filtered and dried to afford Intermediate A5 (18.0 g, 94.2% yield) as a light brown solid.

TLC: Pet. ether/EtOAc=2/1 (v/v), Rf=0.6

Intermediate A6

Synthesis of 2-bromo-6-chloro-4-(dibenzylamino)benzaldehyde (Intermediate A6)

A6

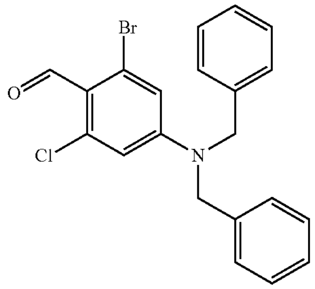

To a solution of Intermediate A5 (10.0 g, 25.9 mmol) in DMF (80 mL), $POCl_3$ (11.9 g, 77.6 mmol) was added dropwise. The reaction mixture was stirred at 90° C. overnight. The reaction mixture was cooled to rt and poured into $NaHCO_3$(aq) (400 mL); the resultant mixture was extracted with EtOAc (100 mL*2). The combined organic phase was washed with brine (400 mL), dried over $Na_2SO_4$, and concentrated in vacuo; the residue was purified by silica gel column chromatography (pet. ether/EtOAc=30/1 to 5/1) to afford Intermediate A6 (5.0 g, 47% yield) as a light brown solid.

TLC: Pet. ether/EtOAc=2/1 (v/v), Rf=0.15

Intermediate A7

Synthesis of (2-bromo-6-chloro-4-(dibenzylamino) phenyl)methanol (Intermediate A7)

A7

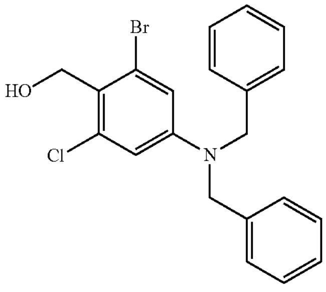

A solution of Intermediate A6 (5.5 g, 13 mmol) in THF (50 mL) was cooled to 0° C. $NaBH_4$ (0.75 g, 20 mmol) was added in portions. The reaction was stirred at rt for 1 h, then quenched with water (60 mL) and extracted with EtOAc (20 mL*2). The combined organic phase was washed with brine (50 mL), dried over $Na_2SO_4$, and concentrated in vacuo. The residue was purified by silica gel column chromatography (pet. ether/EtOAc=10/1 to 3/1) to afford Intermediate A7 (2.5 g, 45% yield) as a yellow solid.

TLC: Pet. ether/EtOAc=1/1 (v/v), Rf=0.10

$^1$H NMR: (400 MHz, DMSO-$d_6$) δ 7.35 (t, J=7.4 Hz, 4H), 7.31-7.21 (m, 6H), 6.82 (d, J=2.5 Hz, 1H), 6.69 (d, J=2.6 Hz, 1H), 4.81 (t, J=5.1 Hz, 1H), 4.74 (s, 4H), 4.52 (d, J=5.1 Hz, 2H).

Intermediate A8

Synthesis of N,N-dibenzyl-3-bromo-5-chloro-4-(chloromethyl)aniline (Intermediate A)

A8

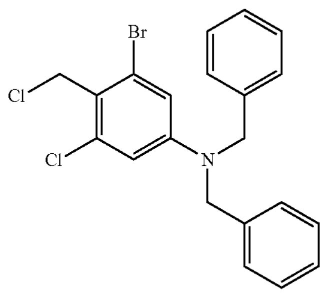

To a solution of Intermediate A7 (2.0 g, 4.8 mmol) in DCM (30 mL) were added a catalytic amount of DMF and $SOCl_2$ (1.14 g, 9.60 mmol). The reaction was stirred at rt for 30 min. The reaction mixture was concentrated in vacuo to afford Intermediate A8 (2.0 g, 96% yield) as a yellow solid.

TLC: Pet. ether/EtOAc=1/1 (v/v), Rf=0.85

Intermediate A9

Synthesis of N-(3,5-dichloro-4-methylphenyl)acetamide (Intermediate A9)

A9

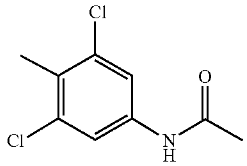

To a solution of 3,5-dichloro-p-toluidine (15.0 g, 85.2 mmol) in DCM (30 mL) was added acetyl chloride (8.0 g, 102 mmol). The mixture was stirred at rt overnight. The reaction mixture was diluted with EtOAc (100 mL), washed with brine (50 mL*2), and dried over $Na_2SO_4$. The crude product was concentrated in vacuo to afford Intermediate A9 (17.0 g, 91.5% yield) as a yellow solid.

TLC: Pet. ether/EtOAc=3/1 (v/v), Rf=0.16.

LCMS: RT=1.959 min, [M−1]=216.0.

$^1$H NMR: (400 MHz, DMSO-$d_6$) δ 10.16 (s, 1H), 7.66 (s, 2H), 2.33 (s, 3H), 2.04 (s, 3H).

Intermediate A10

Synthesis of N-(3,5-dichloro-2-fluoro-4-methylphenyl)acetamide (Intermediate A10)

A10

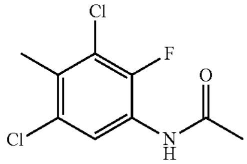

To a solution of Intermediate A9 (7.0 g, 32 mmol) in acetonitrile (100 mL) was added Selectfluor (11.4 g, 32.1 mmol). The mixture was stirred at 80° C. overnight. The reaction mixture was diluted with EtOAc (20 mL); the resultant mixture was washed with brine (10 mL*2) and dried over $Na_2SO_4$. The crude product was concentrated in vacuo and purified by silica gel column chromatography (pet. ether/EtOAc=100/1 to 10/1) to afford Intermediate A10 (1.5 g, 20% yield) as a yellow solid.

TLC: Pet. ether/EtOAc=3/1 (v/v), Rf=0.40.

$^1$H NMR: (400 MHz, DMSO-$d_6$) δ 10.01 (s, 1H), 8.05 (d, J=7.2 Hz, 1H), 2.38 (s, 3H), 2.10 (s, 3H).

Intermediate A11

Synthesis of N-(4-(bromomethyl)-3,5-dichloro-2-fluorophenyl)acetamide (Intermediate A11)

A11

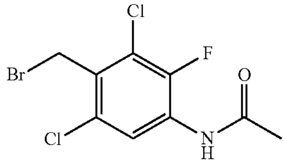

A solution of Intermediate A10 (800 mg, 3.39 mmol), N-bromosuccinimide (844 mg, 4.74 mmol) and benzoyl peroxide (246 mg, 1.02 mmol) in $CCl_4$ (20 mL) was stirred at 50° C. for 15 min, then at 100° C. overnight. The crude product was concentrated in vacuo and purified by silica gel column chromatography (pet. ether/EtOAc=30/1 to 10/1) to afford Intermediate A11 (880 mg, 82.4% yield) as a yellow solid.

TLC: Pet. ether/EtOAc=3/1 (v/v), Rf=0.44.

LCMS: RT=2.135 min, [M+1]=313.9.

$^1$H NMR: (400 MHz, DMSO-$d_6$) δ 10.19 (s, 1H), 8.21 (d, J=6.8 Hz, 1H), 4.76 (d, J=0.8 Hz, 2H), 2.13 (s, 3H).

Intermediate A12

Synthesis of 5-bromo-2-(bromomethyl)-1,3-dichlorobenzene (Intermediate A12)

A12

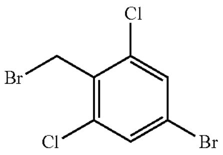

To a solution of 4-bromo-2,6-dichlorotoluene (9.8 g, 41 mmol) in $CCl_4$ (100 mL) at rt were added benzoyl peroxide (495 mg, 2.04 mmol) and N-bromosuccinimide (7.3 g, 41 mmol). The mixture was stirred at 80° C. for 2 h. The mixture was filtered, and the filtrate was diluted with DCM (50 mL). Water (100 mL) was added and the resultant mixture was extracted with DCM (50 mL*2). The organic phase was washed with brine (100 mL), dried over $Na_2SO_4$, concentrated in vacuo and purified by silica gel column chromatography (pet. ether/EtOAc=3/1) to afford Intermediate A12 (12 g, 92% yield) as a light yellow solid.

TLC: Pet. ether/EtOAc=3/1 (v/v), Rf=0.45.

$^1$H NMR: (400 MHz, DMSO-$d_6$) δ 7.87 (s, 2H), 4.74 (s, 2H).

Intermediate B1

Synthesis of 4-iodo-2-isopropylphenol (Intermediate B1)

B1

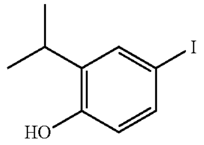

To a solution of 2-isopropylphenol (840 g, 6.17 mol, 1.0 eq) in methanol (10 L) were added NaI (925 g, 6.17 mol, 1.0 eq) and NaOH (247 g, 6.17 mol, 1.0 eq). The mixture was cooled to −10° C. and sodium hypochlorite (9.6 L, 6.2 mol, 15% in water) was added dropwise over 4 h. The mixture was quenched by slowly adding 10% aq. $Na_2S_2O_3$ solution (5 L) with stirring; the mixture was acidified with concentrated aqueous HCl. The mixture was extracted with EtOAc (5 L*2). The combined organic phase was washed with brine (5 L), dried over $Na_2SO_4$, and concentrated in vacuo. The residue was purified by silica gel column chromatography (pet. ether/EtOAc=100/1 to 20/1) to afford Intermediate B1 (800 g, 49% yield) as a reddish oil.

$^1$H NMR: (400 MHz, DMSO-$d_6$) δ 10.08 (s, 1H), 7.85 (d, J=2.3 Hz, 1H), 7.80 (dd, J=8.4, 2.3 Hz, 1H), 7.13 (d, J=8.4 Hz, 1H), 3.64 (m, 1H), 1.64 (d, J=6.9 Hz, 6H).

Intermediate B2

Synthesis of 4-iodo-2-isopropyl-1-(methoxymethoxy)benzene (Intermediate B2)

B2

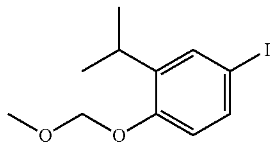

To a solution of Intermediate B1 (283 g, 1.08 mol, 1.0 eq) in DMF (3.28 L) were added MOM-Cl (258 g, 3.24 mol, 3.0 eq) and $Cs_2CO_3$ (1.05 kg, 3.24 mol, 3.0 eq). The mixture was stirred at rt for 3 h under N2 atmosphere. The mixture was diluted with water (10 L) and extracted with EtOAc (5 L*2). The combined organic layers were dried over $Na_2SO_4$ and concentrated in vacuo. The residue was purified by silica gel column chromatography (pet. ether/EtOAc=100/1 to 30/1) to afford Intermediate B2 (250 g, 76% yield) as a reddish oil.

$^1$H NMR: (400 MHz, DMSO-$d_6$) δ7.45 (d, J=8.0 Hz, 2H), 6.87 (d, J=8.0 Hz, 1H), 5.20 (s, 2H), 3.37 (s, 3H), 3.26-3.18 (m, 1H), 1.14 (d, J=8.0 Hz, 6H)

Intermediate B3

Synthesis of 3-fluoro-2-(prop-1-en-2-yl)phenol (Intermediate B3)

B3

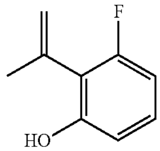

To a mixture of 2-bromo-3-fluorophenol (38.0 g, 200 mmol), isopropenyl-2-boron(pinacolate) (50.4 g, 300 mmol) and Pd(dppf)$Cl_2$·$CH_2Cl_2$ (16 g, 20 mmol) in 1,4-dioxane (300 mL) and water (30 mL) at rt was added $K_2CO_3$ (55.3 g, 400 mmol). The mixture was heated to 70° C. and stirred overnight. The reaction mixture was cooled to rt, quenched with water (100 mL) and extracted with EtOAc (100 mL*3). The combined organic phase was washed with brine (200 mL), dried over $Na_2SO_4$, concentrated in vacuo and purified by silica gel column chromatography (EtOAc/pet. ether=1/100 to 1/20) to afford Intermediate B3 (23 g, 76% yield) as white solid.

TLC: EtOAc/pet. ether=1/10 (v/v), Rf=0.55

$^1$H NMR: (400 MHz, DMSO-$d_6$) δ 9.72 (s, 1H), 7.06 (td, J=8.4, 6.8 Hz, 1H), 6.66 (td, J=8.4, 1.2 Hz, 1H), 6.59 (m, 1.0 Hz, 1H), 5.28 (m, 1H), 4.89 (m, 1H), 1.98 (s, 3H).

Intermediate B4

Synthesis of 3-fluoro-2-isopropylphenol (Intermediate B4)

B4

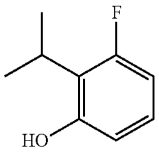

To a solution of Intermediate B3 (23.0 g, 151 mmol) in MeOH (300 mL) was added Pd/C (10%) (6.0 g). The reaction mixture was stirred at 60° C. overnight. The mixture was cooled to 0° C., filtered, and concentrated in vacuo to afford Intermediate B4 (21 g, 90% yield) as a yellow oil.

TLC: EtOAc/pet. ether=1/50 (v/v), $R_f$=0.25

$^1$H NMR: (400 MHz, DMSO-$d_6$) δ 9.69 (s, 1H), 7.00-6.93 (m, 1H), 6.65-6.60 (m, 1H), 6.52 (ddd, J=10.8, 8.0, 1.2 Hz, 1H), 3.40 (m, 1H), 1.25 (dd, J=7.2, 1.2 Hz, 6H).

Intermediate B5

Synthesis of 2-(3-(difluoromethoxy)phenyl)-4,4,5,5-tetramethyl-1,3,2-dioxaborolane (Intermediate B5)

B5

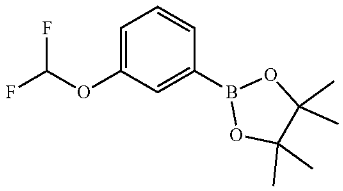

A mixture of (3-bromophenyl)-difluoromethyl ether (3.0 g, 13 mmol), bis(pinacolato)diboron (6.8 g, 27 mmol), Pd(dppf)$Cl_2$ (984 mg, 1.35 mmol) and KOAc (4.0 g, 40 mmol) in dry 1,4-dioxane (30 mL) was stirred at 85° C. overnight. The resultant solution of Intermediate B5 was used without further purification.

TLC: EtOAc/pet. ether=1/2 (v/v), Rf=0.2

Intermediate B6

Synthesis of 3'-(difluoromethoxy)-[1,1'-biphenyl]-2-ol (Intermediate B6)

B6

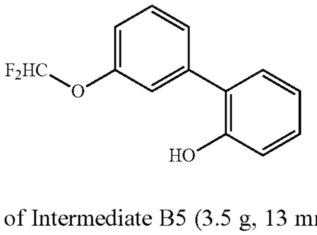

A mixture of Intermediate B5 (3.5 g, 13 mmol), 2-bromophenol (1.5 g, 8.67 mmol), Pd(dppf)$Cl_2$ (634 mg, 0.87 mmol) and $K_2CO_3$ (3.6 g, 26 mmol) in 1,4-dioxane (30 mL) and water (3 mL) was stirred at 90° C. overnight. Water (50 mL) was added, and the mixture was extracted with EtOAc (30 mL*2). The combined organic phase was washed with brine (50 mL), dried over $Na_2SO_4$, and concentrated in vacuo. The residue was purified by silica gel column chromatography (pet. ether/EtOAc=20/1 to 5/1, v/v) to afford Intermediate B6 (700 mg, 34% yield) as a yellow oil.

TLC: EtOAc/pet. ether=1/5 (v/v), Rf=0.54

LCMS: RT=2.551 min; [M−1]=235.0

Intermediate B7

Synthesis of 2-((4-fluorophenyl)(hydroxy)methyl)phenol (Intermediate B7)

B7

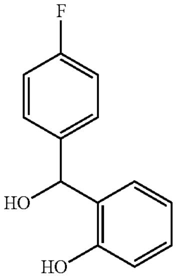

To a solution of 2-bromophenol (4.18 g, 24.2 mmol) in THF (40 mL) at −30° C. was added dropwise n-BuLi (2.5 M in hexanes) (29.0 mmol, 11.6 mL). After 0.5 h, 4-fluorobenzaldehyde (3.0 g, 24.2 mmol) in THF (10 mL) was added dropwise. The mixture was stirred for 1 h, then quenched with saturated aqueous $NH_4Cl$ (50 mL), acidified with 1N HCl to pH-6-7 and extracted with EtOAc (10 mL*3). The combined organic phase was washed with brine (15 mL), dried over $Na_2SO_4$, and concentrated in vacuo. The crude product was purified by silica gel column chromatography (pet. ether/EtOAc=20/1 to 5/1) to afford Intermediate B7 (2.5 g, 46% yield) as a yellow oil.

TLC: EtOAc/pet. ether=1/5 (v/v), Rf=0.36

$^1$H NMR: (400 MHz, DMSO-$d_6$) δ 9.43 (s, 1H), 7.36 (td, J=5.6, 2.4 Hz, 3H), 7.14-6.97 (m, 3H), 6.82-6.70 (m, 2H), 5.96 (d, J=4.2 Hz, 1H), 5.72 (d, J=4.3 Hz, 1H).

Intermediate B8

Synthesis of 2-(4-fluorobenzyl)phenol (Intermediate B8)

B8

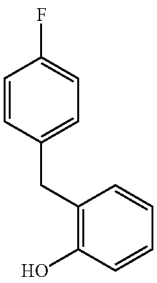

To a solution of Intermediate B7 (2.47 g, 11.3 mmol) in DCM (25 mL) at rt was added $Et_3SiH$ (5.26 g, 45.3 mmol). The mixture was stirred at 0° C. for 10 min, then TFA (38.7 g, 340 mmol) was added dropwise. The mixture was stirred at rt for 3 h, diluted with DCM (20 mL) and concentrated in vacuo. The crude product was purified by silica gel column chromatography (pet. ether/EtOAc=50/1 to 10/1) to afford Intermediate B8 (1.9 g, 81% yield) as a yellow oil.

TLC: EtOAc/pet. ether=1/5 (v/v), $R_f$=0.64

$^1$H NMR: (400 MHz, DMSO-$d_6$) δ 9.39 (s, 1H), 7.25-7.20 (m, 2H), 7.10-6.98 (m, 4H), 6.81-6.78 (m, 1H), 6.71 (td, J=7.4, 1.3 Hz, 1H), 3.84 (s, 2H).

Intermediate C1

Synthesis of (2,6-dichloro-4-(dibenzylamino)phenyl)(3-isopropyl-4-(methoxymethoxy)phenyl)methanol (Intermediate C1)

C1

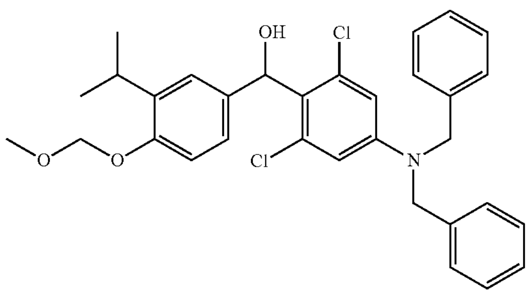

A solution of Intermediate B2 (1.1 g, 3.5 mmol) in THF (10 mL) was cooled to −20° C.; iPr-MgCl (2.7 mL of 2M solution in THF, 5.4 mmol) was added dropwise. The mixture was stirred at rt for 2 h. The mixture was cooled to −78° C. and Intermediate A2 (1.0 g, 2.70 mmol) in THF (4 mL) was added dropwise. The resultant mixture was stirred at −78° C. for 2 h. Aqueous $NH_4Cl$ (30 mL) was added to quench reaction, and the mixture was extracted with EtOAc (10 mL*3). The combined organic layers were washed with brine (30 mL), dried over $Na_2SO_4$, and concentrated in vacuo to give a brown oil. The crude product was purified by silica gel column chromatography (pet. ether/EtOAc=30:1) to afford Intermediate C1 (700 mg, 47% yield) as a colorless oil.

TLC: Pet. ether/EtOAc=5/1 (v/v), Rf=0.5

$^1$H NMR: (400 MHz, DMSO-$d_6$) δ 7.38-7.32 (m, 4H), 7.26 (t, J=6.6 Hz, 7H), 6.92-6.81 (m, 2H), 6.65 (s, 2H), 6.25 (d, J=4.4 Hz, 1H), 5.74 (t, J=5.6 Hz, 1H), 5.15 (s, 2H), 4.74 (s, 4H), 3.37 (s, 3H), 3.25-3.19 (m, 1H), 1.12 (t, J=6.4 Hz, 6H).

Intermediate C2

Synthesis of (4-amino-2,6-dichlorophenyl)(3-isopropyl-4-(methoxymethoxy)phenyl)methanol (Intermediate C2)

C2

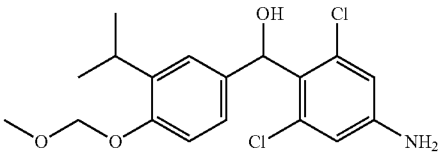

To a solution of Intermediate C1 (2.1 g, 3.8 mmol) in THF (20 mL) was added Pd/C (400 mg). The mixture was degassed in vacuo and purged with $H_2$ three times. The mixture was stirred under $H_2$ gas (1 atmosphere) at rt for 2 h. The mixture was filtered and concentrated in vacuo to afford Intermediate C2 (1.4 g, 97% yield) as a gray solid.

TLC: Pet. ether/EtOAc=3/1 (v/v), Rf=0.3

$^1$H NMR: (400 MHz, DMSO-$d_6$) δ 7.23 (s, 1H), 6.90 (d, J=1.2 Hz, 2H), 6.57 (s, 2H), 6.23 (s, 1H), 5.17 (s, 2H), 3.27-3.22 (m, 1H), 1.13 (t, J=6.8 Hz, 6H).

Intermediate C3

Synthesis of 4-(4-amino-2,6-dichlorobenzyl)-2-isopropylphenol (Intermediate C3)

C3

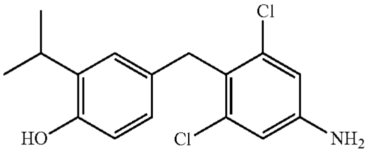

To a solution of Intermediate C2 (1.0 g, 2.70 mmol) in DCM (10 mL) at 0° C. was added $Et_3SiH$ (14 mmol, 1.6 g); TFA (81 mmol, 9.2 g) was added dropwise to the resultant solution. The mixture was stirred at rt overnight, then concentrated in vacuo to remove solvent. Water (20 mL) was added and the resultant mixture was extracted with EtOAc (20 mL*3). The combined organic layer was washed with brine (30 mL), dried over $Na_2SO_4$, and concentrated in vacuo to give a yellow oil. The crude product was purified by silica gel column chromatography (pet. ether/EtOAc=20:1) to afford Intermediate C3 (200 mg, 24% yield) as a yellow solid.

TLC: Pet. ether/EtOAc=3/1 (v/v), Rf=0.4

$^1$H NMR: (400 MHz, DMSO-$d_6$) δ 9.02 (s, 1H), 6.95 (s, 1H), 6.72-6.57 (m, 4H), 5.53 (s, 2H), 3.92 (s, 2H), 3.16-3.09 (m, 1H), 1.10 (d, J=6.8 Hz, 6H).

Intermediate C4

Synthesis of 4-(2,6-dichloro-4-(dibenzylamino)benzyl)-3-fluoro-2-isopropylphenol (Intermediate C4)

C4

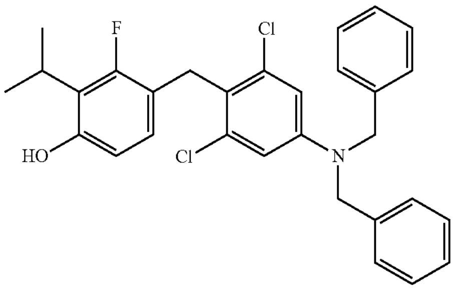

To a solution of Intermediate B4 (7.6 g, 20 mmol) in DCE (40 mL) at rt were added Intermediate A4 (6.0 g, 39 mmol) and $ZnCl_2$ (39 mL of a 1.0M solution in THF, 39 mmol). The mixture was stirred at 75° C. for 16 h. The reaction mixture was cooled to rt, water (50 mL) was added, and the resultant mixture was extracted with DCM (50 mL*2). The combined organic phase was washed with brine, dried over $Na_2SO_4$, and concentrated in vacuo; the residue was purified by silica gel column chromatography (pet. ether/EtOAc=30/1 to 5/1) to afford Intermediate C4 (4.5 g, 46%) as a yellow solid.

TLC: Pet. ether/EtOAc=1/1 (v/v), Rf=0.3

$^1$H NMR: (400 MHz, DMSO-$d_6$) δ 9.47 (s, 1H), 7.36 (s, 4H), 7.25 (s, 6H), 6.73 (s, 2H), 6.46 (d, J=8.4 Hz, 1H), 6.27 (t, J=8.6 Hz, 1H), 4.74 (s, 4H), 3.89 (s, 2H), 3.40-3.34 (m, 1H), 1.24 (s, 7H).

Intermediate C5

Synthesis of 4-(4-amino-2,6-dichlorobenzyl)-3-fluoro-2-isopropylphenol (Intermediate C5)

C5

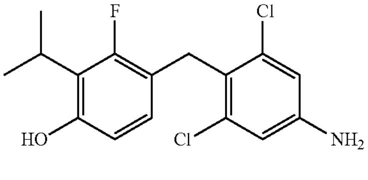

To a solution of Intermediate C4 (4.5 g, 8.8 mmol) in THF (50 mL) at rt was added Pd/C (1.0 g). The mixture was stirred at 35° C. under 1 atmosphere of $H_2$ pressure for 1 h. The reaction mixture was cooled to rt, filtered and concentrated in vacuo to afford the Intermediate C5 (2.3 g, 79%) as a yellow solid.

TLC: Pet. ether/EtOAc=1/1 (v/v), Rf=0.3

$^1$H NMR: (400 MHz, DMSO-$d_6$) δ 9.46 (s, 1H), 6.65 (s, 2H), 6.48 (s, 1H), 6.29 (s, 1H), 5.61 (s, 2H), 3.90 (s, 2H), 3.38 (d, J=7.1 Hz, 1H), 1.26 (s, 7H).

Intermediate C6

Synthesis of 5-(2,6-dichloro-4-(dibenzylamino)benzyl)-3'-(difluoromethoxy)-[1,1'-biphenyl]-2-ol (Intermediate C6)

C6

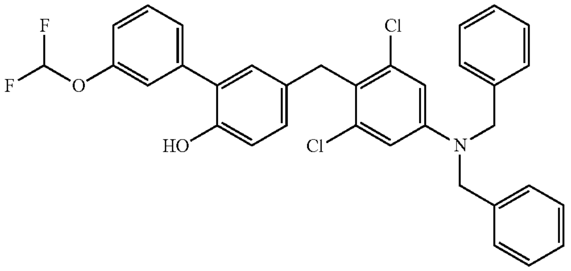

A solution of Intermediate A4 (827 mg, 2.12 mol), Intermediate B6 (1.0 g, 4.2 mol) and $ZnCl_2$ (5.3 mL of a 1.0M solution in THF, 5.3 mmol) in DCE (20 mL) was stirred at 85° C. overnight. The mixture was cooled to rt, washed with water (20 mL), dried over $Na_2SO_4$, concentrated in vacuo, and purified by silica gel column chromatography (pet. ether/EtOAc=5/1, v/v) to afford Intermediate C6 (1.0 g, 80% yield) as a colorless oil.

TLC: EtOAc/pet. ether=1/5 (v/v), Rf=0.39

$^1$H NMR: (400 MHz, DMSO-$d_6$) δ 9.50 (s, 1H), 7.46-7.39 (m, 1H), 7.37-7.31 (m, 5H), 7.25 (ddd, J=7.7, 6.1, 1.9 Hz, 8H), 7.12-7.04 (m, 2H), 6.92 (dd, J=8.3, 2.3 Hz, 1H), 6.83 (d, J=8.3 Hz, 1H), 6.71 (s, 2H), 4.72 (s, 4H), 3.99 (s, 2H).

Intermediate C7

Synthesis of 5-(4-amino-2,6-dichlorobenzyl)-3'-(difluoromethoxy)-[1,1'-biphenyl]-2-ol (Intermediate C7)

C7

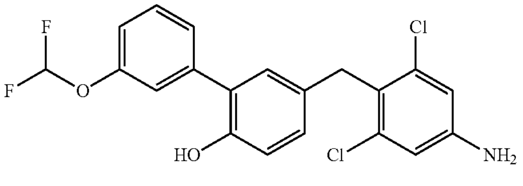

A mixture of Intermediate C6 (1.1 g, 1.9 mmol) and Pd/C (200 mg) in THF (20 mL) was degassed in vacuo and purged three times with $H_2$ gas, and the mixture was stirred at rt overnight under 1 atm of $H_2$ gas. The mixture was filtered, then concentrated in vacuo to afford Intermediate C7 (750 mg, 98% yield) as a brown solid.

TLC: EtOAc/pet. ether=1/1 (v/v), Rf=0.44

$^1$H NMR: (400 MHz, DMSO-$d_6$) δ 9.49 (s, 1H), 7.46-7.40 (m, 1H), 7.34-7.28 (m, 2H), 7.24 (d, J=0.6 Hz, 1H), 7.09 (dd, J=8.0, 2.6 Hz, 1H), 7.05 (d, J=2.4 Hz, 1H), 6.92 (dd, J=8.3, 2.3 Hz, 1H), 6.84 (d, J=8.2 Hz, 1H), 6.64 (s, 2H), 3.99 (s, 2H).

Intermediate C8

Synthesis of 4-(2,6-dichloro-4-(dibenzylamino)benzyl)-2-(4-fluorobenzyl)phenol (Intermediate C8)

C8

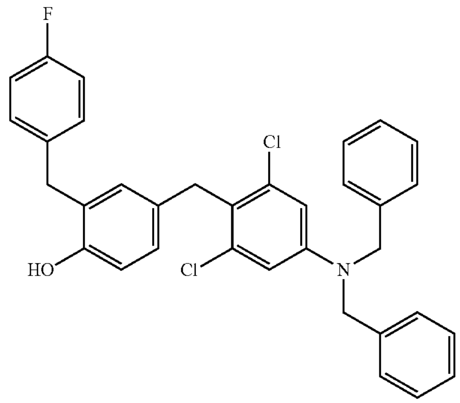

A solution of Intermediate A4 (966 mg, 2.47 mmol), Intermediate B8 (1.0 g, 5.0 mmol) and $ZnCl_2$ (842 mg, 6.18 mmol) in DCE (10 mL) was stirred at 85° C. overnight. The mixture was washed with water (20 mL), and brine (20 mL), dried over $Na_2SO_4$, concentrated in vacuo and purified by silica gel column chromatography (pet. ether/EtOAc=50/1, v/v) to afford Intermediate C8 (1.0 g, 73% yield) as a colorless oil.

TLC: EtOAc/pet. ether=1/10 (v/v), Rf=0.4

$^1$H NMR: (400 MHz, DMSO-$d_6$) δ 9.21 (s, 1H), 7.38-7.32 (m, 4H), 7.28-7.22 (m, 6H), 7.19-7.14 (m, 2H), 7.06-6.99 (m, 2H), 6.83 (d, J=2.2 Hz, 1H), 6.72 (dd, J=8.2, 2.4 Hz, 1H), 6.69-6.64 (m, 3H), 4.72 (s, 4H), 3.87 (s, 2H), 3.76 (s, 2H).

Intermediate C9

Synthesis of 4-(4-amino-2,6-dichlorobenzyl)-2-(4-fluorobenzyl)phenol (Intermediate C9)

C9

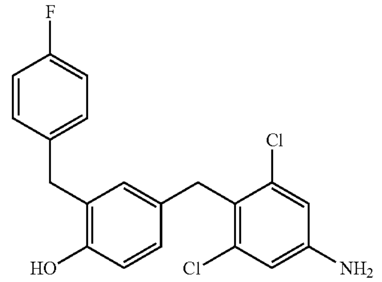

A mixture of Intermediate C8 (1.0 g, 1.8 mmol) and Pd/C (109 mg) in THF (20 mL) was stirred at rt overnight under a blanket of $H_2$ gas. The mixture was filtered and concentrated in vacuo to afford Intermediate C9 (670 mg, 99% yield) as a brown solid.

TLC: EtOAc/pet. ether=1/3 (v/v), Rf=0.35

$^1$H NMR: (400 MHz, DMSO-$d_6$) δ 9.19 (s, 1H), 7.22-7.16 (m, 2H), 7.09-7.01 (m, 2H), 6.85 (d, J=2.2 Hz, 1H), 6.72 (dd, J=8.2, 2.2 Hz, 1H), 6.67 (d, J=8.2 Hz, 1H), 6.61 (s, 2H), 5.53 (s, 2H), 3.88 (s, 2H), 3.78 (s, 2H).

Intermediate C10

Synthesis of 4-(2-bromo-6-chloro-4-(dibenzylamino)benzyl)-2-isopropylphenol (Intermediate C10)

C10

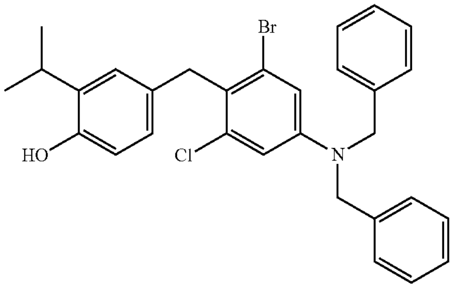

To a solution of Intermediate A8 (2.0 g, 4.60 mmol) and 2-isopropylphenol (1.8 g, 14 mmol) in DCE (30 mL) was added $ZnCl_2$ (1M in THF, 11.5 mL). The reaction was stirred at 75° C. overnight. The reaction was cooled to rt, water (50 mL) was added, and the resultant mixture was extracted with DCM (20 mL*2). The combined organic phase was washed with brine (40 mL), dried over $Na_2SO_4$, and concentrated in vacuo; the residue was purified by silica gel column chromatography (pet. ether/EtOAc=30/1 to 5/1) to afford Intermediate C10 (1.8 g, 73% yield) as a yellow oil.

TLC: Pet. ether/EtOAc=1/1 (v/v), Rf=0.15

$^1$H NMR: (400 MHz, DMSO-$d_6$) δ 9.01 (d, J=1.2 Hz, 1H), 7.35 (t, J=7.5 Hz, 4H), 7.29-7.19 (m, 6H), 6.97-6.86 (m, 2H), 6.75 (t, J=1.9 Hz, 1H), 6.68-6.58 (m, 2H), 4.72 (s, 4H), 3.96 (s, 2H), 3.18-3.05 (m, 1H), 1.09 (dd, J=7.0, 1.3 Hz, 6H).

Intermediate C11

Synthesis of 4-(2-chloro-4-(dibenzylamino)-6-(prop-1-en-2-yl)benzyl)-2-isopropylphenol (Intermediate C11)

C11

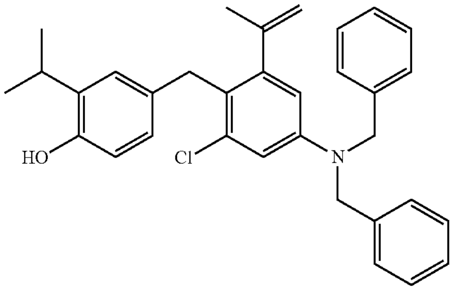

To a solution of Intermediate C10 (1.3 g, 2.4 mmol) in 1,4-dioxane (10 mL) and water (2 mL) were added potassium isopropenyltrifluoroborate (0.54 g, 3.7 mmol), Pd(dppf)$Cl_2$ (180 mg, 0.24 mmol) and $K_2CO_3$ (1.01 g, 7.2 mmol). The reaction was stirred at 90° C. overnight. The reaction mixture was cooled to rt, water (50 mL) was added and the resultant mixture was extracted with EtOAc (20 mL*2). The combined organic phase was washed with water (50 mL) and brine (50 mL), dried over $Na_2SO_4$, and concentrated in vacuo. The residue was purified by silica gel column chromatography (pet. ether/EtOAc=20/1 to 5/1) to afford Intermediate C11 (0.40 g, 33% yield) as a yellow solid.

TLC: Pet. ether/EtOAc=1/1 (v/v), Rf=0.3

$^1$H NMR: (400 MHz, DMSO-$d_6$) δ 8.95 (s, 1H), 7.37-7.30 (m, 4H), 7.29-7.20 (m, 6H), 6.74 (d, J=2.1 Hz, 1H), 6.63 (d, J=2.7 Hz, 1H), 6.60-6.52 (m, 2H), 6.41 (d, J=2.8 Hz, 1H), 5.02 (s, 1H), 4.69 (s, 4H), 4.60 (s, 1H), 3.81 (s, 2H), 3.10 (p, J=6.9 Hz, 1H), 1.06 (d, J=6.9 Hz, 6H).

Intermediate C12

Synthesis of 4-(4-amino-2-chloro-6-isopropylbenzyl)-2-isopropylphenol (Intermediate C12)

C12

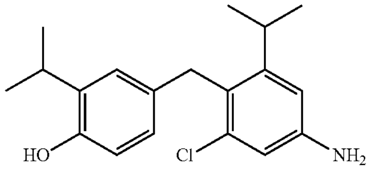

To a solution of Intermediate C11 (496 mg, 1.0 mmol) in THF (10 mL) was added Pd/C (100 mg). The reaction mixture was stirred under 1 atm of hydrogen gas overnight. The mixture was filtered and concentrated in vacuo; the residue was purified by silica gel column chromatography (pet. ether/EtOAc=10/1 to 3/1) to afford Intermediate C12 (150 mg, 47% yield) as a yellow solid.

TLC: Pet. ether/EtOAc=1/1 (v/v), Rf=0.1

Intermediate C13

Synthesis of N-(3,5-dichloro-2-fluoro-4-(4-hydroxy-3-isopropylbenzyl)phenyl)acetamide (Intermediate C13)

C13

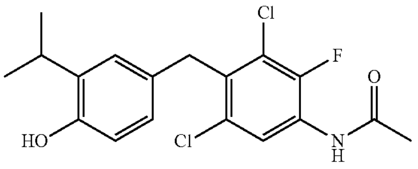

To a solution of Intermediate A11 (800 mg, 2.54 mmol) in DCE (5 mL) at rt were added 2-isopropylphenol (692 mg, 5.08 mmol) and $ZnCl_2$ (865 mg, 6.35 mmol). The reaction mixture was heated to 90° C. and stirred overnight. The reaction mixture was diluted with DCM (30 mL), washed with brine (20 mL*2), dried over $Na_2SO_4$, and concentrated in vacuo. The residue was purified by Prep-TLC (pet. ether/EtOAc=5/1) to afford Intermediate C13 (180 mg, 19% yield) as a yellow solid.

TLC: Pet. ether/EtOAc=5/1 (v/v), Rf=0.24.

LCMS: RT=1.672 min, [M−1]=367.9.

$^1$H NMR: (400 MHz, DMSO-$d_6$) δ 9.11 (s, 1H), 8.11 (d, J=6.8 Hz, 1H), 6.99 (d, J=2.0 Hz, 1H), 6.68 (dd, J=8.4, 2.0 Hz, 1H), 6.65 (d, J=8.4 Hz, 2H), 4.09 (s, 2H), 3.13 (m, 1H), 2.12 (s, 3H), 1.11 (d, J=6.8 Hz, 6H).

Intermediate C14

Synthesis of 4-(4-amino-2,6-dichloro-3-fluorobenzyl)-2-isopropylphenol (Intermediate C14)

C14

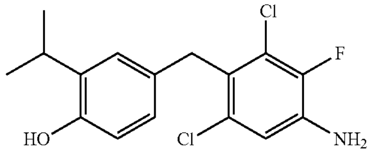

To a solution of Intermediate C13 (180 mg, 0.49 mmol) in water (1 mL) and THF (3 mL) was added NaOH (194 mg, 4.86 mmol). The mixture was stirred at 100° C. overnight. The reaction mixture was diluted with water (20 mL), acidified with 2N HCl to pH-6-8, and extracted with EtOAc (20 mL*2). The combined organic phase was washed with brine (10 mL*2), dried over $Na_2SO_4$, and concentrated in vacuo; the residue was purified by Prep-HPLC to afford Intermediate C14 (66 mg, 41% yield) as a yellow solid.

TLC: Pet. ether/EtOAc=3/1 (v/v), Rf=0.48.

LCMS: RT=1.864 min, [M+1]=328.0.

$^1$H NMR: (400 MHz, DMSO-$d_6$) δ 9.06 (s, 1H), 6.95 (d, J=1.6 Hz, 1H), 6.84 (d, J=8.0 Hz, 1H), 6.66 (dd, J=8.4, 2.0 Hz, 1H), 6.63 (d, J=8.0 Hz, 1H), 3.95 (s, 2H), 3.12 (p, J=6.8 Hz, 1H), 1.10 (d, J=6.8 Hz, 6H).

Intermediate C15 Synthesis of 4-(4-bromo-2,6-dichlorobenzyl)-3-fluoro-2-isopropylphenol (Intermediate C15)

C15

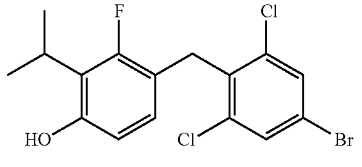

A mixture of Intermediate A12 (500 mg, 1.57 mmol), Intermediate B4 (725 mg, 4.71 mmol) and $Zn(OTf)_2$ (2.8 g, 7.85 mmol) was microwaved at 160° C. with stirring for 2 h. The reaction mixture was diluted with DCM (5 mL), washed with brine (5 mL*2), dried over $Na_2SO_4$, concentrated in vacuo and purified by Prep-TLC (EtOAc/pet. ether=1/10) to afford Intermediate C15 (120 mg, 19% yield) as a brown oil.

TLC: Pet. ether/EtOAc=5/1 (v/v), Rf=0.21

$^1$H NMR: (400 MHz, DMSO-$d_6$) δ 9.56 (s, 1H), 7.83 (s, 2H), 6.48 (d, J=8.4 Hz, 1H), 6.29 (t, J=8.8 Hz, 1H), 4.07 (s, 2H), 3.38 (d, J=7.2 Hz, 1H), 1.25 (d, J=7.2 Hz, 6H).

Intermediate C16

Synthesis of 4-(4-bromo-2,6-dichlorobenzyl)-2-isopropylphenol (Intermediate C16)

C16

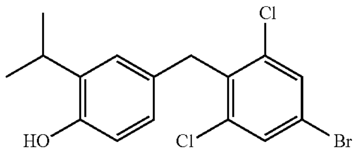

To a solution of Intermediate A12 (1.5 g, 4.7 mmol) in chlorobenzene (10 mL) at rt were added 2-isopropylphenol (1.92 g, 14.1 mmol) and $Zn(OTf)_2$ (5.13 g, 14.1 mmol). The reaction mixture microwaved at 150° C. with stirring for 1 h. The mixture was cooled to rt and concentrated in vacuo. The residue was purified by silica gel column chromatography (pet. ether/EtOAc=100/1 to 20/1) to afford Intermediate C16 (0.40 g, 23%) as a yellow oil.

TLC: Pet. ether/EtOAc=5/1 (v/v), Rf=0.15

$^1$H NMR: (400 MHz, DMSO-$d_6$) δ 9.14 (s, 1H), 7.80 (s, 2H), 6.99 (d, J=1.9 Hz, 1H), 6.70-6.61 (m, 2H), 4.10 (s, 2H), 3.14 (p, J=6.9 Hz, 1H), 1.11 (d, J=6.9 Hz, 6H).

Intermediate C17

Synthesis of 2-(4-(4-bromo-2,6-dichlorobenzyl)-2-isopropylphenoxy)tetrahydro-2H-pyran (Intermediate C17)

C17

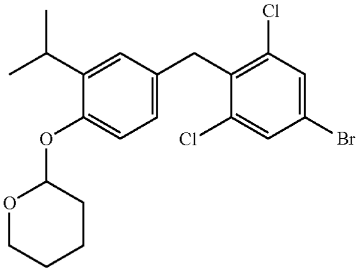

To solution of Intermediate C16 (1.2 g, 3.2 mmol) in THF (15 mL) were added 3,4-Dihydro-2H-pyran (324 mg, 3.85 mmol), and PPTS (151 mg, 3.85 mmol). The reaction mixture was stirred at rt overnight. Water (30 mL) was added, and the resultant mixture was extracted with EtOAc (15 mL*2). The combined organic phase was washed with brine (30 mL), dried over $Na_2SO_4$, and concentrated in vacuo. The residue was purified by silica gel column chromatography (pet. ether/EtOAc=1 to 30/1) to afford Intermediate C17 (1.2 g, 82% yield).

TLC: Pet. ether/EtOAc=10/1 (v/v), Rf=0.75

$^1$H NMR: (400 MHz, DMSO-$d_6$) δ 7.81 (s, 2H), 7.07 (d, J=2.3 Hz, 1H), 6.93 (d, J=8.5 Hz, 1H), 6.80 (dd, J=8.4, 2.3 Hz, 1H), 5.40 (s, 1H), 4.14 (s, 2H), 3.71 (s, 1H), 3.51 (s, 1H), 3.21 (d, J=20.7 Hz, 1H), 1.77 (d, J=15.7 Hz, 3H), 1.59 (dd, J=37.3, 10.5 Hz, 4H), 1.15 (dd, J=6.9, 5.2 Hz, 6H).

Intermediate C18

Synthesis of methyl (E)-3-(3,5-dichloro-4-(3-isopropyl-4-((tetrahydro-2H-pyran-2-yl)oxy)benzyl)phenyl)acrylate (Intermediate C18)

C18

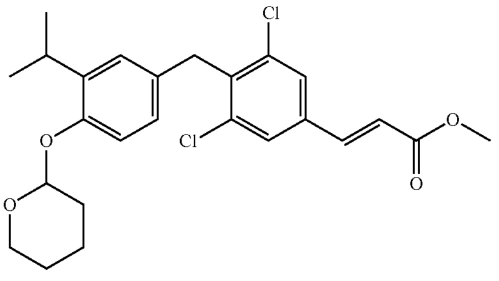

To a solution of Intermediate C17 (200 mg, 0.43 mmol) in DMF (5 mL) were added methyl acrylate (74 mg, 0.86 mmol), $Pd(OAc)_2$ (10 mg, 43 μmol), and $K_2CO_3$ (120 mg, 0.86 mmol). The reaction mixture was heated to 100° C. overnight. The mixture was cooled to rt, water (30 mL) was added, and the resultant mixture was extracted with EtOAc (30 mL*2). The combined organic phase was washed with brine (50 mL), dried over $Na_2SO_4$, and concentrated in vacuo; the residue was purified by silica gel column chromatography (pet. ether/EtOAc=100/1 to 10/1) to afford Intermediate C18 (100 mg, 49% yield) as a light yellow oil.

TLC: Pet. ether/EtOAc=1/1 (v/v), Rf=0.25

$^1$H NMR: (400 MHz, DMSO-$d_6$) δ 7.93 (s, 2H), 7.62 (d, J=16.0 Hz, 1H), 7.09 (d, J=2.2 Hz, 1H), 6.93 (d, J=8.5 Hz, 1H), 6.86-6.77 (m, 2H), 5.39 (s, 1H), 4.18 (s, 2H), 3.73 (s, 4H), 3.51 (d, J=6.8 Hz, 1H), 3.26-3.16 (m, 1H), 1.76 (d, J=19.6 Hz, 3H), 1.68-1.44 (m, 3H), 1.14 (dd, J=6.8, 5.3 Hz, 6H).

Intermediate C19

Synthesis of methyl 3-(3,5-dichloro-4-(4-hydroxy-3-isopropylbenzyl)phenyl)-3-oxopropanoate (Intermediate C19)

C19

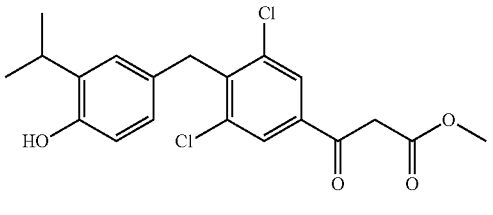

To Intermediate C18 (100 mg, 0.21 mmol) in ethanol (5 mL) were added $FeCl_2$ (3.0 mg, 21 μmol) and polymethylhydrosiloxane (140 mg, 0.63 mmol). The reaction was stirred at 80° C. for 3 h. The reaction mixture was cooled to rt and concentrated in vacuo, and the residue was purified by Prep-TLC (pet. ether/EtOAc=2/1) to afford Intermediate C19 (30 mg, 36% yield) as a light yellow oil.

TLC: Pet. ether/EtOAc=2/1 (v/v), Rf=0.15

$^1$H NMR: (400 MHz, DMSO-$d_6$) δ 9.16 (s, 1H), 8.01 (s, 2H), 7.02 (d, J=2.1 Hz, 1H), 6.74-6.60 (m, 2H), 4.29 (s, 2H), 4.20 (s, 2H), 3.65 (s, 3H), 3.13 (p, J=6.9 Hz, 1H), 1.10 (d, J=6.9 Hz, 6H).

Intermediate D1

Synthesis of 2,6-difluoro-3-(4,4,5,5-tetramethyl-1,3,2-dioxaborolan-2-yl)phenol (Intermediate D1)

D1

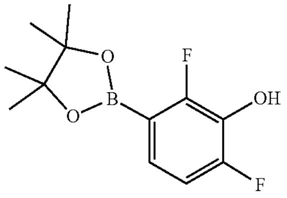

To a mixture of 3-bromo-2,6-difluorophenol (300 mg, 1.44 mmol), bis(pinacolato)diboron (401 mg, 1.58 mmol) and Pd(dppf)$Cl_2$ (52 mg, 72 μmol) in 1,4-dioxane (15 mL) was added potassium acetate (423 mg, 4.31 mmol). The mixture was heated to 100° C. and stirred for 3 h. The mixture was cooled to rt and filtered. The filtrate was concentrated in vacuo to afford crude Intermediate D1 (300 mg, 82% yield), which was used without further purification.

TLC: Pet. ether/EtOAc=3/1 (v/v), Rf=0.90.

Example 1

Synthesis of 2-(3,5-dichloro-4-(4-hydroxy-3-isopropylbenzyl)phenyl)-5-hydroxy-3-oxo-2,3-dihydro-1,2,4-triazine-6-carbonitrile (Compound 1)

1

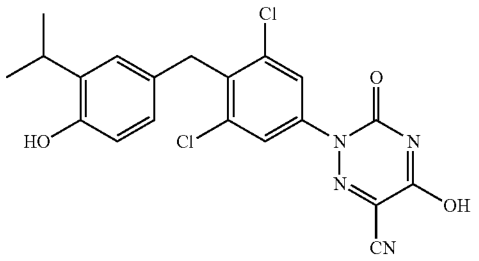

A solution of Intermediate C3 (5.0 g, 16.1 mmol) in acetonitrile (20 mL)/water (100 mL) and conc. aqueous HCl (110 mL) was cooled to 0° C.; a solution of $NaNO_2$ (1.3 g, 19.3 mmol) in water (10 mL) was added dropwise. The mixture was stirred at 0° C. for 1 h. This mixture was added dropwise to a solution of ethyl N-(2-cyanoacetyl)carbamate (2.8, 17.7 mmol) in water (100 mL) and pyridine (125 mL), stirring at 0° C. After 1 h, the reaction mixture was extracted with EtOAc (100 mL*2); the combined organic phase was washed with brine (50 mL*2), dried over $Na_2SO_4$, and concentrated in vacuo. The resultant crude product (7.6 g of a yellow oil) was dissolved in HOAc (50 mL); NaOAc (6.5, 79.6 mmol) was added, and the mixture was stirred at 100° C. for 2 h. The reaction mixture was cooled to rt; water (100 mL) was added, and the mixture was extracted with EtOAc (50 mL*3). The combined organic phase was washed with brine (50 mL*2), dried over $Na_2SO_4$, and concentrated in vacuo; the residue was purified by reversed-phase Prep-HPLC to provide Compound 1 (1.5 mg, 21.2% yield) as a yellow solid.

TLC: DCM/MeOH=1/1 (v/v), Rf=0.1

LCMS: RT=4.31 min, [M−1]=447.0

$^1$H NMR: (400 MHz, DMSO-$d_6$) δ 9.59 (d, J=1.4 Hz, 2H), 7.67 (s, 4H), 6.51 (d, J=8.3 Hz, 2H), 6.33 (t, J=8.6 Hz, 2H), 4.15 (s, 4H), 3.39 (d, J=7.2 Hz, 3H), 2.07 (s, 1H), 1.26 (d, J=7.0 Hz, 12H)

Example 2

Synthesis of 2-(3,5-dichloro-4-(2-fluoro-4-hydroxy-3-isopropylbenzyl)phenyl)-5-hydroxy-3-oxo-2,3-dihydro-1,2,4-triazine-6-carbonitrile (Compound 2)

2

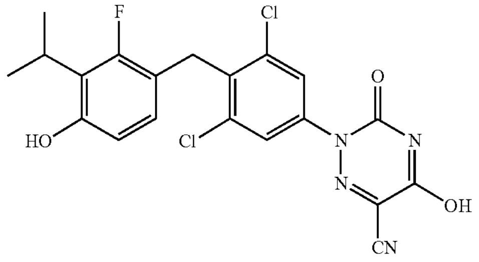 [SMILES: CC(C)c1c(O)ccc(Cc2c(Cl)cc(-n3nc(C#N)c(O)nc3=O)cc2Cl)c1F]

A solution of Intermediate C5 (270 mg, 0.82 mmol) in water (10 mL) and conc. aqueous HCl (10 mL) was cooled to 0° C., and a solution of $NaNO_2$ (68 mg, 0.98 mmol) in water (1 mL) was added dropwise. The mixture was stirred at 0° C. for 30 min. This mixture was added dropwise to a solution of ethyl N-(2-cyanoacetyl)carbamate (140 mg, 0.86 mmol) in water (10 mL) and pyridine (15 mL), and stirred at 0° C. After 1 h, the mixture was extracted with EtOAc (10 mL*2). The combined organic phase was washed with brine (30 mL), dried over $Na_2SO_4$ and concentrated in vacuo. The crude product was dissolved in HOAc (8 mL) and NaOAc (337 mg, 4.11 mmol) was added. The resultant mixture was stirred at 100° C. for 2 h. The reaction mixture was cooled to rt, water (30 mL) was added, and the mixture was extracted with EtOAc (10 mL*2). The combined organic phase was washed with brine (30 mL), dried over $Na_2SO_4$, and concentrated in vacuo; the residue was purified by Prep-HPLC to afford Compound 2 (6.0 mg, 1.6% yield).

TLC: DCM/MeOH=1/1 (v/v), Rf=0.1

LCMS: RT=4.31 min, [M−1]=447.0

$^1$H NMR: (400 MHz, DMSO-$d_6$) δ 9.59 (d, J=1.4 Hz, 2H), 7.67 (s, 4H), 6.51 (d, J=8.3 Hz, 2H), 6.33 (t, J=8.6 Hz, 2H), 4.15 (s, 4H), 3.39 (d, J=7.2 Hz, 3H), 2.07 (s, 1H), 1.26 (d, J=7.0 Hz, 12H)

Example 3

Synthesis of 2-(3,5-dichloro-4-((3'-(difluoromethoxy)-6-hydroxy-[1,1'-biphenyl]-3-yl)methyl)phenyl)-5-hydroxy-3-oxo-2,3-dihydro-1,2,4-triazine-6-carbonitrile (Compound 3)

3

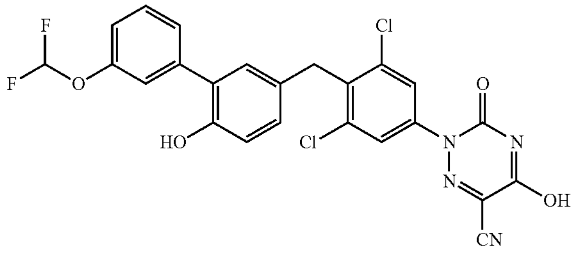 [SMILES: N#Cc1nn(-c2cc(Cl)c(Cc3ccc(O)c(-c4cccc(OC(F)F)c4)c3)c(Cl)c2)c(=O)nc1O]

A solution of intermediate C7 (400 mg, 0.97 mmol) in conc. aqueous HCl (7 mL) and water (7 mL) was cooled to 0° C., and a solution of $NaNO_2$ (81 mg, 1.17 mmol) in water (1 mL) was added dropwise. The mixture was stirred at 0° C. for 30 min. This mixture was added dropwise to a solution of ethyl N-(2-cyanoacetyl)carbamate (167 mg, 1.07 mmol) in water (7 mL) and pyridine (10 mL), stirring at 0° C. After 1 h the mixture was extracted with EtOAc (50 mL*2); the combined organic phase was washed with brine (50 mL), dried over $Na_2SO_4$, and concentrated in vacuo. A mixture of this material (500 mg, 0.87 mmol) and NaOAc (355 mg, 4.33 mmol) in HOAc (5 mL) was stirred at 100° C. for 2 h. The mixture was cooled to rt; water (30 mL) was added, and the mixture was extracted with EtOAc (25 mL). The combined organic phase was washed with water (20 mL*3), then brine (50 mL), dried over $Na_2SO_4$, concentrated in vacuo, and purified twice by Prep-TLC (DCM/MeOH=10/1) to afford Compound 3 (20 mg, 4.4% yield) as a yellow solid.

TLC: MeOH/DCM=1/5 (v/v), Rf=0.32

LCMS: RT=1.787 min, [M−1]=528.8

$^1$H NMR: (400 MHz, DMSO-$d_6$) δ 13.19 (s, 1H), 9.61 (s, 1H), 7.67 (s, 2H), 7.44 (t, J=7.9 Hz, 1H), 7.35 (dt, J=7.8, 1.2 Hz, 1H), 7.31 (t, J=2.0 Hz, 1H), 7.24 (t, J=74.2 Hz, 1H), 7.15 (d, J=2.3 Hz, 1H), 7.10 (dd, J=8.0, 2.5 Hz, 1H), 6.95 (dd, J=8.4, 2.3 Hz, 1H), 6.88 (d, J=8.3 Hz, 1H), 4.25 (s, 2H).

Example 4

Synthesis of 2-(3,5-dichloro-4-(3-(4-fluorobenzyl)-4-hydroxybenzyl)phenyl)-5-hydroxy-3-oxo-2,3-dihydro-1,2,4-triazine-6-carbonitrile (Compound 4)

4

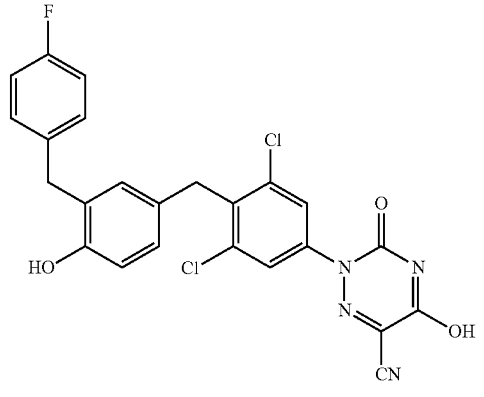 [SMILES: N#Cc1nn(-c2cc(Cl)c(Cc3ccc(O)c(Cc4ccc(F)cc4)c3)c(Cl)c2)c(=O)nc1O]

A solution of Intermediate C9 (490 mg, 1.30 mmol) in conc. aqueous HCl (15 mL) and water (15 mL) was cooled to 0° C.; a solution of $NaNO_2$ (108 mg, 1.56 mmol) in water (1 mL) was added dropwise. The mixture was stirred at 0° C. for 30 min, then added dropwise to a solution of ethyl N-(2-cyanoacetyl)carbamate (224 mg, 1.43 mmol) in water (15 mL) and pyridine (15 mL), stirring at 0° C. After 1 h the mixture was extracted with EtOAc (50 mL*2). The combined organic phase was washed with brine (50 mL), dried over $Na_2SO_4$, and concentrated in vacuo. A mixture of this intermediate (600 mg, 1.10 mmol) and NaOAc (453 mg, 5.52 mmol) in HOAc (10 mL) was stirred at 100° C. for 2 h. Water (30 mL) was added, and the mixture was extracted with EtOAc (25 mL*2). The combined organic layer was washed with water (40 mL*3), then brine (50 mL), dried over $Na_2SO_4$, and purified twice by Prep-TLC (DCM/MeOH=10/1) to afford Compound 4 (16 mg, 2.7% yield) as a yellow solid.

TLC: MeOH/DCM=1/5 (v/v), Rf=0.32

LCMS: RT=3.626 min, [M−1]=494.9

$^1$H NMR: (400 MHz, DMSO-$d_6$) δ 13.21 (s, 1H), 9.32 (s, 1H), 7.63 (s, 2H), 7.19 (dd, J=8.4, 5.8 Hz, 2H), 7.09-7.02 (m, 2H), 6.90 (d, J=2.2 Hz, 1H), 6.77 (dd, J=8.4, 2.2 Hz, 1H), 6.71 (d, J=8.2 Hz, 1H), 4.13 (s, 2H), 3.80 (s, 2H).

Example 5

Synthesis of 2-(3-chloro-4-(4-hydroxy-3-isopropylbenzyl)-5-isopropylphenyl)-5-hydroxy-3-oxo-2,3-dihydro-1,2,4-triazine-6-carbonitrile (Compound 5)

5

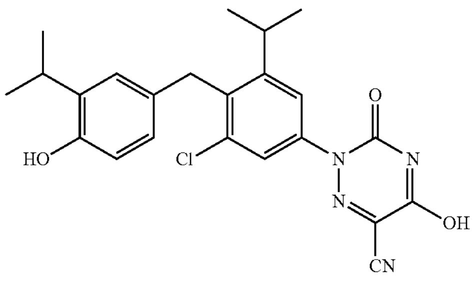 [SMILES: CC(C)c1cc(Cc2c(Cl)cc(-n3nc(C#N)c(O)nc3=O)cc2C(C)C)ccc1O]

A solution of Intermediate C12 (200 mg, 0.63 mmol) in water (5 mL) and con. HCl (5 mL) was cooled to 0° C.; $NaNO_2$ (52 mg, 0.75 mmol) in water (1 mL) was added dropwise. The mixture was stirred at 0° C. for 30 min, then added dropwise to a mixture of ethyl N-(2-cyanoacetyl)carbamate (98 mg, 0.63 mmol) in water (5 mL) and pyridine (5 mL) at 0° C. After 1 h, the mixture was extracted with EtOAc (10 mL*2). The combined organic phase was washed with brine (30 mL), dried over $Na_2SO_4$, and concentrated in vacuo. This material was dissolved in HOAc (5 mL); NaOAc (258 mg, 3.15 mmol) was added, and the resultant mixture was stirred at 100° C. for 2 h. The reaction mixture was cooled to rt, water (30 mL) was added, and the resultant mixture was extracted with EtOAc (10 mL*2). The combined organic phase was washed with brine (30 mL), dried over $Na_2SO_4$, and concentrated in vacuo; the residue was purified by Prep-HPLC to afford Compound 5 (35 mg, 12% yield).

TLC: DCM/MeOH=1/1 (v/v), Rf=0.1

LCMS: RT=2.62 min, [M−1]=437.0

$^1$H NMR: (400 MHz, DMSO-$d_6$) δ 13.04 (s, 1H), 9.10 (s, 1H), 7.45 (dd, J=20.6, 2.2 Hz, 2H), 6.88 (d, J=2.1 Hz, 1H), 6.72-6.52 (m, 2H), 4.25-4.04 (m, 2H), 3.18 (dq, J=28.4, 6.8 Hz, 2H), 1.08 (dd, J=9.6, 6.7 Hz, 12H).

Example 6

Synthesis of 2-(3,5-dichloro-2-fluoro-4-(4-hydroxy-3-isopropylbenzyl)phenyl)-5-hydroxy-3-oxo-2,3-dihydro-1,2,4-triazine-6-carbonitrile (Compound 6)

6

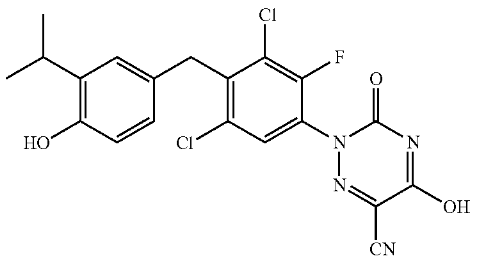 [SMILES: CC(C)c1cc(Cc2c(Cl)cc(-n3nc(C#N)c(O)nc3=O)c(F)c2Cl)ccc1O]

A solution of Intermediate C14 (360 mg, 1.10 mmol) in con. HCl (7 mL) and water (7 mL) was cooled to 0° C.; $NaNO_2$ (91 mg, 1.3 mmol) in water (1 mL) was added dropwise. The resultant mixture was stirred at 0° C. for 30 min, then added to a cooled solution of ethyl N-(2-cyano-acetyl)carbamate (188 mg, 1.21 mmol) in water (7 mL) and pyridine (10 mL). This mixture was stirred at 0° C. for 1 h, then extracted with EtOAc (20 mL*2). The combined organic phase was washed with brine (50 mL), dried over $Na_2SO_4$, and concentrated in vacuo. The residue was combined with NaOAc (355 mg, 4.33 mmol) in AcOH (5 mL) and stirred at 100° C. for 2 h. The mixture was cooled to rt; water (30 mL) was added, and the mixture was extracted with EtOAc (25 mL). The organic layer was washed with water (20 mL*3), then brine (50 mL), dried over $Na_2SO_4$, and purified by Prep-HPLC to afford Compound 6 (20 mg, 7.4% yield) as a yellow solid.

TLC: MeOH/DCM=1/5 (v/v), Rf=0.36

LCMS: RT=1.749 min, [M−1]=447.0

$^1$H NMR: (400 MHz, DMSO-$d_6$) δ 13.27 (s, 1H), 9.18 (s, 1H), 7.74 (d, J=6.6 Hz, 1H), 7.05 (d, J=2.1 Hz, 1H), 6.73-6.65 (m, 2H), 4.21 (s, 2H), 3.14 (p, J=6.9 Hz, 1H), 1.12 (d, J=6.9 Hz, 6H).

Example 7

Synthesis of 3',5'-dichloro-3,5-difluoro-4'-(2-fluoro-4-hydroxy-3-isopropylbenzyl)-[1,1'-biphenyl]-4-ol (Compound 7)

7

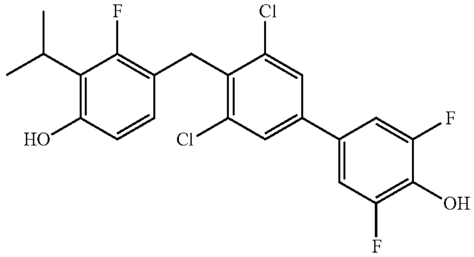 [SMILES: CC(C)c1c(O)ccc(Cc2c(Cl)cc(-c3cc(F)c(O)c(F)c3)cc2Cl)c1F]

To a solution of Intermediate C15 (25 mg, 64 μmol) and 3,5-difluoro-4-hydroxyphenylboronic acid (17 mg, 96 μmol) in 1,4-dioxane/water (10/1 mL) at rt were added Pd(dppf)$Cl_2$ (5.0 mg, 6.4 μmol) and $NaHCO_3$ (16 mg, 0.19 mmol). The reaction mixture was purged with nitrogen and heated overnight at 80° C. The reaction mixture was diluted with EtOAc (5 mL), washed with brine (10 mL*2), dried over $Na_2SO_4$, concentrated in vacuo and purified by Prep-HPLC to afford Compound 7 (7.0 mg, 25% yield) as a yellow solid.

TLC: Pet. ether/EtOAc=3/1 (v/v), Rf=0.31.

LCMS: RT=3.538 min, [M−1]=439.1.

$^1$H NMR: (400 MHz, DMSO-$d_6$) δ 10.53 (s, 1H), 9.55 (s, 1H), 7.86 (s, 2H), 7.58 (dd, J=8.4, 1.6 Hz, 2H), 6.48 (d, J=8.0 Hz, 1H), 6.32 (t, J=8.8 Hz, 1H), 4.12 (s, 2H), 3.41 (d, J=7.2 Hz, 1H), 1.26 (d, J=6.8 Hz, 6H).

Example 8

Synthesis of 3',5'-dichloro-2,4-difluoro-4'-(2-fluoro-4-hydroxy-3-isopropylbenzyl)-[1,1'-biphenyl]-3-ol (Compound 8)

8

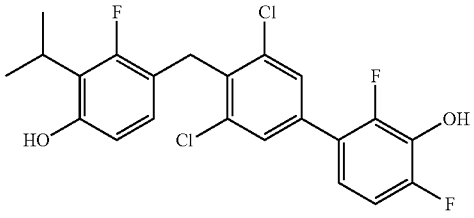 [SMILES: CC(C)c1c(O)ccc(Cc2c(Cl)cc(-c3ccc(F)c(O)c3F)cc2Cl)c1F]

To a solution of Intermediate D1 (60 mg, 0.15 mmol) and Intermediate C15 (59 mg, 0.23 μmol) in 1,4-dioxane (10 mL) at rt were added Pd(dppf)$Cl_2$ (11 mg, 15.30 μmol) and aqueous $NaHCO_3$ (2M, 0.23 mL). The reaction was heated to 80° C. overnight under a nitrogen atmosphere. The reaction mixture was diluted with EtOAc (10 mL), washed with brine (10 mL*2), dried over $Na_2SO_4$, and concentrated in vacuo. The crude product was purified by Prep-HPLC to afford Compound 8 (25 mg, 37% yield) as a brown solid.

TLC: Pet. ether/EtOAc=3/1 (v/v), Rf=0.23.

LCMS: RT=3.486 min, [M−1]=439.0.

$^1$H NMR: (400 MHz, DMSO-$d_6$) δ 10.44 (s, 1H), 9.57 (d, J=1.2 Hz, 1H), 7.65 (d, J=1.2 Hz, 2H), 7.15-7.12 (m, 1H), 7.08-7.00 (m, 1H), 6.51 (d, J=6.8 Hz, 1H), 6.36 (t, J=8.4 Hz, 1H), 4.14 (s, 2H), 3.40-3.37 (m, 1H), 1.27 (d, J=7.2 Hz, 6H).

Example 9

Synthesis of 5-(3,5-dichloro-4-(4-hydroxy-3-isopropylbenzyl)phenyl)isoxazol-3-ol (Compound 9)

9

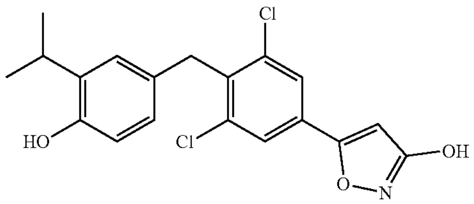 [SMILES: CC(C)c1cc(Cc2c(Cl)cc(-c3cc(O)no3)cc2Cl)ccc1O]

To a solution of hydroxylamine hydrochloride (26 mg, 0.375 mmol) and NaOH (30 mg, 0.75 mmol) in $MeOH/H_2O$ (5/2 mL) was added Intermediate C19 (100 mg, 0.25 mmol). The mixture was stirred at rt for 2 h. Water (20 mL) was added, the pH of the solution was adjusted to pH~3-4 with 1N HCl, and the resultant mixture was extracted with EtOAc (10 mL*2). The combined organic phase was washed with brine (20 mL), dried over $Na_2SO_4$, and concentrated in vacuo; the residue was purified by Prep-HPLC to afford Compound 9 (10 mg, 10% yield) as a light brown solid.

TLC: DCM/MeOH=15/1 (v/v), Rf=0.15

LCMS: RT=4.18 min, [M−1]=376.0)

$^1$H NMR: (400 MHz, DMSO-$d_6$) δ 9.15 (s, 1H), 7.86 (s, 2H), 7.01 (s, 1H), 6.68 (q, J=8.3 Hz, 2H), 5.80 (s, 1H), 4.17 (s, 2H), 3.14 (s, 1H), 1.10 (d, J=6.9 Hz, 6H).

Example 10

Synthesis of 2-(3,5-dichloro-4-((3'-(difluoromethoxy)-6-hydroxy-[1,1'-biphenyl]-3-yl)methyl)phenyl)-5-hydroxy-1,2,4-triazin-3(2H$_1$-one (Compound 10)

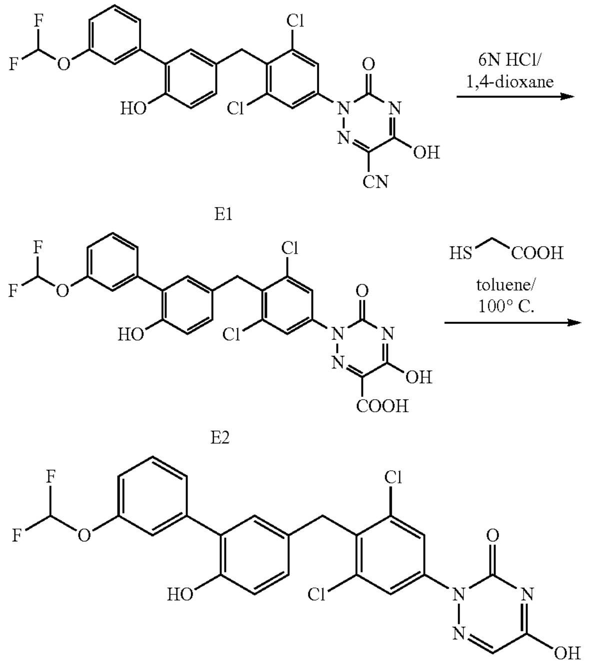

E1

E2

10

A mixture of compound E1 (120 mg, 226 μmol) in 1,4-dioxane (2 mL) and HCl (12 M, 2 mL) was stirred at 60° C. for 8 h. The mixture was quenched with $H_2O$ (10 mL) and extracted with EtOAc (5 mL*2). The combined organic layer was washed with water (15 mL*2), brine (10 mL), dried over $Na_2SO_4$, and concentrated to dryness to afford product compound 2 (100 mg, 80.5% yield) as a yellow solid.

To a mixture of compound E2 (120 mg, 218 μmol) in toluene (3 mL) was added mercaptoacetic acid (40 mg, 436 μmol). The mixture was stirred at 110° C. for 48 h. The mixture was quenched with $H_2O$ (10 mL) and extracted with EtOAc (10 mL). The organic layer was washed with water (25 mL*2), brine (50 mL), dried over $Na_2SO_4$, concentrated to dryness, and purified by Prep-HPLC to afford Compound 10 (15 mg, 13.4% yield) as a yellow solid.

LCMS: RT=1.66 min, [M−1]=503.9

Example 11

Thyroid-Hormone Reporter-Gene Assays

Compounds were tested for thyroid-hormone receptor activity using TR reporter-gene assays. Reporter cells used in the assays express a TR-receptor hybrid (either TRα or TRβ) in which the native N-terminal DNA binding domain (DBD) has been replaced with that of the yeast Gal4 DBD. The reporter gene, firefly luciferase, is functionally linked to the Gal4 upstream activation sequence (UAS). Both cell lines were derived from human embryonic kidney (HEK293).

Step 1: A suspension of reporter cells was prepared in cell recovery medium containing 10% charcoal-stripped FBS, and dispensed into assay plates. The plates were pre-incubated for 6 hours in a cell culture incubator (37° C./5% CO2/85% humidity).

Step 2: Test compound master stocks and triiodothyronine were diluted in DMSO to generate solutions at "1,000×-concentration" relative to each final treatment concentration. These intermediate stocks were subsequently diluted directly into compound screening medium containing 10% charcoal-stripped FBS to generate "2×-concentration" treatment media (containing 0.2, 0.4 or 0.8% DMSO).

Step 3: At the end of the pre-incubation period, culture media were discarded from the assay plates, and all wells received 100 μl of compound screening medium. 100 μl of each of the previously prepared "2×-concentration" treatment media were dispensed into duplicate assay wells, thereby achieving the desired final treatment concentrations. The final concentration of DMSO in all assay wells was 0.1, 0.2 or 0.4%. Assay plates were incubated for 24 hr in a cell culture incubator (37° C./5% CO2/85% humidity).

Step 4: At the 24 h assay endpoint, treatment media were discarded and 100 μl/well of luciferase detection reagent was added. Relative luminometer units (RLUs) were quantified from each assay well. The performance of the TRα and TRβ assays was validated using the reference agonist triiodothyronine (T3).

The results of these assays are presented in Table 2 below, wherein data are reported as $EC_{50}$ values determined for TRα and TRβ receptors, and the selectivity index (SI) is calculated as $EC_{50}$ (TRa)/$EC_{50}$ (TRs). To this end, $EC_{50}$ and SI values are expressed as follows:

Potency: +$EC_{50}$>1,000 nM

++100 nM<$EC_{50}$≤1,000 nM

+++10 nM<$EC_{50}$≤100 nM

++++$EC_{50}$≤10 nM

ND Not determined

Selectivity: +T3-SI≤3×

++3×<T3-SI≤30×

+++T3-SI>30×

ND Not determined

TABLE 2

| Activity Data | | | |
|---|---|---|---|
| Compound No. | TRα | TRβ | T3-SI |
| T3 | ++++ | +++ | + |
| 1 | ++ | +++ | +++ |
| 2 | +++ | +++ | ++ |
| 3 | + | ++ | +++ |
| 4 | + | ++ | ++ |
| 5 | +++ | ++++ | ++ |
| 6 | ++ | ++ | ++ |
| 7 | + | ++ | ++ |
| 8 | + | + | ND |
| 9 | ++ | +++ | ++ |
| 10 | ++++ | ++++ | ++ |

As indicated by the above experiments, compounds of the present invention show improved TRO3 selectivity when compared to the natural agonist T3. Some also show improved potency when compared to T3.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the structure of Formula (I):

(I)

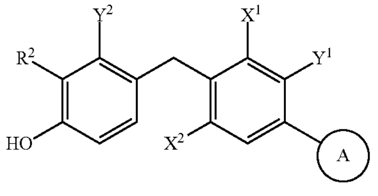

or a tautomer, hydrate, solvate, isotope, or pharmaceutically acceptable salt thereof, wherein:

A is;

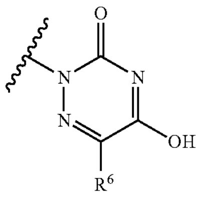

or

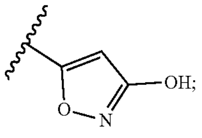

$R^6$ is H or —CN;

$X^1$ is lower alkyl, lower alkenyl, lower haloalkyl, or halo, $X^2$ is lower alkyl, lower alkenyl, lower haloalkyl, or halo;

$Y^1$ is H, —CN, halogen, lower alkyl, or lower alkoxy;

$Y^2$ is H, —CN, halogen, lower alkyl, or lower alkoxy;

$R^2$ is lower alkyl, lower alkenyl, carbocycle, heterocycle, carbocyclealkyl, or heterocyclealkyl, wherein $R^2$ is optionally substituted with one or more halo, lower alkyl, lower haloalkyl, —CN, —OR', —NR'R", =O, =S, —$S(O)_2R'$ or —$S(O)_2OR'$; and R' and R" are each, independently, H, lower alkyl, or lower haloalkyl.

2. The compound of claim 1, or a tautomer, hydrate, solvate, isotope, or pharmaceutically acceptable salt thereof, wherein $R^2$ is unsubstituted lower alkyl.

3. The compound of claim 1, or a tautomer, hydrate, solvate, isotope, or pharmaceutically acceptable salt thereof, wherein $R^2$ is isopropyl.

4. The compound of claim 1, or a tautomer, hydrate, solvate, isotope, or pharmaceutically acceptable salt thereof, wherein:

A is

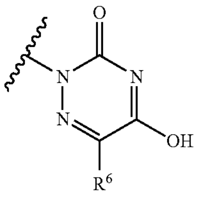

or

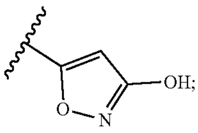

and $R^6$ is —CN.

5. The compound of claim 1, or a pharmaceutically acceptable tautomer, hydrate, solvate, isotope, or salt thereof, wherein A is

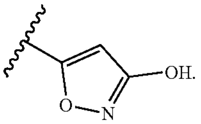 [SMILES: *c1cc(O)no1]

6. The compound of claim 1, or a pharmaceutically acceptable tautomer, hydrate, solvate, isotope, or salt thereof, wherein $X^1$ is lower alkyl or halo, and $X^2$ is halo.

7. The compound of claim 1, or a pharmaceutically acceptable tautomer, hydrate, solvate, isotope, or salt thereof, wherein $X^1$ is halo.

8. The compound of claim 1, or a tautomer, hydrate, solvate, isotope, or pharmaceutically acceptable salt thereof, wherein $Y^1$ is H and $Y^2$ is halogen.

9. The compound of claim 1, or a tautomer, hydrate, solvate, isotope, or pharmaceutically acceptable salt thereof, wherein $Y^1$ is halogen and $Y^2$ is H.

10. The compound of claim 1, or a tautomer, hydrate, solvate, isotope, or pharmaceutically acceptable salt thereof, wherein $Y^1$ is H and $Y^2$ is H.

11. The compound of claim 1, or a tautomer, hydrate, solvate, isotope, or pharmaceutically acceptable salt thereof, having the structure:

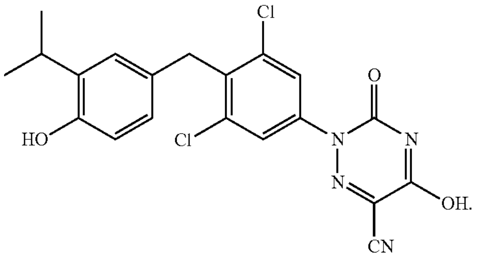 [SMILES: CC(C)c1cc(Cc2c(Cl)cc(-n3nc(C#N)c(O)nc3=O)cc2Cl)ccc1O]

12. The compound of claim 1, or a tautomer, hydrate, solvate, isotope, or pharmaceutically acceptable salt thereof, having the structure:

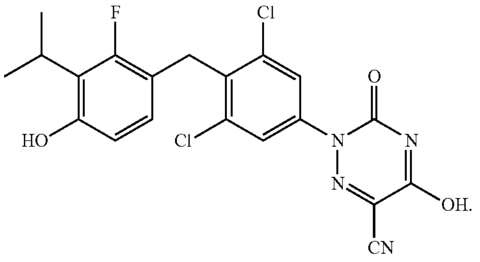 [SMILES: CC(C)c1c(O)ccc(Cc2c(Cl)cc(-n3nc(C#N)c(O)nc3=O)cc2Cl)c1F]

13. The compound of claim 1, or a tautomer, hydrate, solvate, isotope, or pharmaceutically acceptable salt thereof, having the structure:

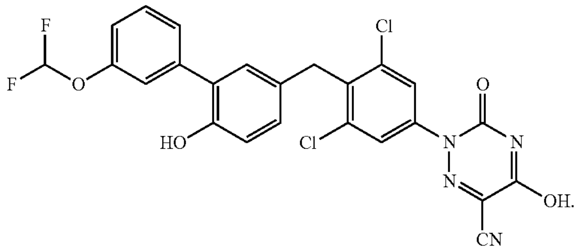 [SMILES: N#Cc1nn(-c2cc(Cl)c(Cc3ccc(O)c(-c4cccc(OC(F)F)c4)c3)c(Cl)c2)c(=O)nc1O]

14. The compound of claim 1, or a tautomer, hydrate, solvate, isotope, or pharmaceutically acceptable salt thereof, having the structure:

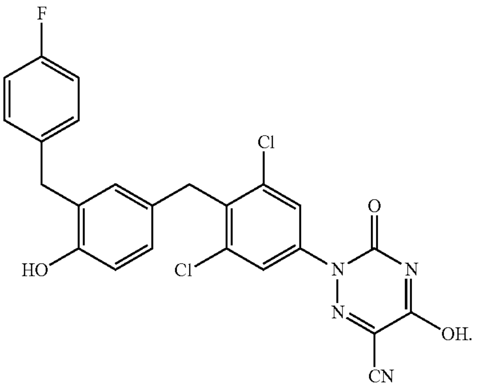 [SMILES: N#Cc1nn(-c2cc(Cl)c(Cc3ccc(O)c(Cc4ccc(F)cc4)c3)c(Cl)c2)c(=O)nc1O]

15. The compound of claim 1, or a tautomer, hydrate, solvate, isotope, or pharmaceutically acceptable salt thereof, having the structure:

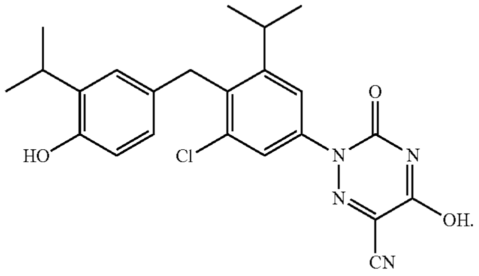 [SMILES: CC(C)c1cc(Cc2c(Cl)cc(-n3nc(C#N)c(O)nc3=O)cc2C(C)C)ccc1O]

16. The compound of claim 1, or a tautomer, hydrate, solvate, isotope, or pharmaceutically acceptable salt thereof, having the structure:

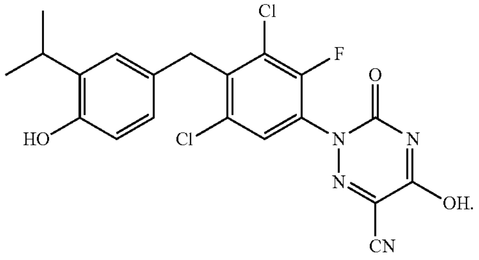 [SMILES: CC(C)c1cc(Cc2c(Cl)cc(-n3nc(C#N)c(O)nc3=O)c(F)c2Cl)ccc1O]

17. The compound of claim 1, or a tautomer, hydrate, solvate, isotope, or pharmaceutically acceptable salt thereof, having the structure:

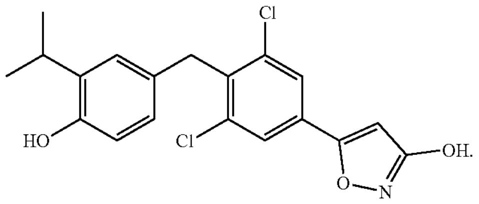 [SMILES: CC(C)c1cc(Cc2c(Cl)cc(-c3cc(O)no3)cc2Cl)ccc1O]

18. The compound of claim 1, or a tautomer, hydrate, solvate, isotope, or pharmaceutically acceptable salt thereof, having the structure:

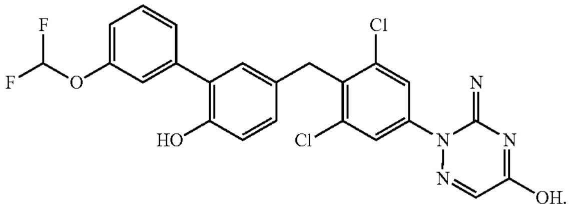 [SMILES: N=c1nc(O)cnn1-c1cc(Cl)c(Cc2ccc(O)c(-c3cccc(OC(F)F)c3)c2)c(Cl)c1]

19. A pharmaceutical composition comprising a compound of claim 1, or a tautomer, hydrate, solvate, isotope, or pharmaceutically acceptable salt thereof, and a pharmaceutically acceptable excipient.

20. A method of modulating thyroid hormone receptor activity in a subject comprising administering to the subject in need thereof a pharmaceutically effective amount of a compound of claim 1, or a pharmaceutically acceptable salt thereof.

* * * * *